US006639674B2

(12) United States Patent
Sokolov et al.

(10) Patent No.: US 6,639,674 B2
(45) Date of Patent: Oct. 28, 2003

(54) METHODS AND APPARATUS FOR POLARIZED REFLECTANCE SPECTROSCOPY

(75) Inventors: Konstantin Sokolov, Austin, TX (US); Rebekah Drezek, Houston, TX (US); Urs Utzinger, Austin, TX (US); Rebecca Richards-Kortum, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 5 days.

(21) Appl. No.: 09/821,836

(22) Filed: Mar. 28, 2001

(65) Prior Publication Data

US 2002/0135752 A1 Sep. 26, 2002

Related U.S. Application Data

(60) Provisional application No. 60/192,540, filed on Mar. 28, 2000.

(51) Int. Cl.[7] .................................................. G01J 4/00
(52) U.S. Cl. ...................................................... 356/369
(58) Field of Search .............................. 356/364, 369, 356/445; 436/63, 64

(56) References Cited

U.S. PATENT DOCUMENTS

| | | | | |
|---|---|---|---|---|
| 4,679,939 A | * | 7/1987 | Curry et al. ................ | 356/336 |
| 5,017,497 A | * | 5/1991 | Gerard de Grooth et al. . | 436/63 |
| 5,056,918 A | * | 10/1991 | Bott et al. ................... | 356/336 |
| 5,104,221 A | * | 4/1992 | Bott et al. ................... | 356/336 |
| 5,164,787 A | * | 11/1992 | Igushi et al. ................ | 356/336 |
| 5,369,496 A | * | 11/1994 | Alfano et al. ............... | 356/446 |
| 6,052,187 A | * | 4/2000 | Krishnan et al. ............ | 356/369 |
| 6,067,157 A | * | 5/2000 | Altendorf .................... | 356/337 |
| 6,307,633 B1 | * | 10/2001 | Mandella et al. ............ | 356/479 |
| 6,320,656 B1 | * | 11/2001 | Ferrante et al. ............. | 356/339 |
| 6,404,494 B1 | * | 6/2002 | Masonis et al. ............. | 356/338 |

OTHER PUBLICATIONS

Anderson, "Polarized Light Examination and Photography of the Skin," *Arch. Dermatol.*, 127:1000–1005, 1991.

Artacho–Perula et al., "Histomorphometry of Normal and Abnormal Cervical Samples," *Analyt. Quant. Cytol. Histol.*, 15(4):290–297, 1993.

Asano and Sato, "Light Scattering by Randomly Oriented Spheroidal Particles," *Appl. Opt.*, 19(6):962–974, 1980.

Backman et al., "Polarized Light Scattering Spectroscopy for Quantitative Measurements of Epithelial Cellular Structures In Situ," *IEEE, J. Selected Topics in Quantum Electronics on Lasers in Medicine and Biology* 5(4):1019, 1022–1023, 1026, 1999.

(List continued on next page.)

*Primary Examiner*—Michael P. Stafira
*Assistant Examiner*—Juan D Valentin, II
(74) *Attorney, Agent, or Firm*—Fulbright & Jaworski, LLP

(57) ABSTRACT

Methods and apparatus for assessing the size of a scattering element of a sample. Primary radiation is generated from a source. The primary radiation is polarized to produce polarized primary radiation. The polarized primary radiation is directed to the sample to generate reflected radiation. The reflected radiation is directed through a polarizer to produce filtered reflected radiation, the polarizer being configured to select reflected radiation parallel and perpendicular to the polarization of the polarized primary radiation. The filtered radiation is detected, and a depolarization ratio is calculated using the detected filtered radiation. The size of the scattering element is calculated using the depolarization ratio.

25 Claims, 12 Drawing Sheets

OTHER PUBLICATIONS

Barer, "Refractometry and Interferometry of Living Cells," *J. Opt. Soc. Am.* 47, 545–56 (1957).

Bartel and Hielscher, "Monte Carlo simulations of the diffuse backscattering Mueller matrix for highly scattering media," *Applied Optics*, 39(10):1580–1588, 2000.

Berchuck et al., "Epidermal Growth Factor Receptor Expression in Normal Ovarian Epithelium and Ovarian Cancer. I. Correlation of Receptor Expression with Prognostic factors in Patients with Ovarian Cancer," *Am. J. Obstet. Gynecol.*, 164:669–674, 1991.

Bicout et al., "Depolarization of Multiply Scattered Waves by Spherical Diffusers: Influence of the Size Parameter," *Phys. Rev. E*, 49(2):1767–1770, 1994.

Bigio and Mourant, "Ultraviolet and Visible Spectroscopies for Tissue Diagnostics: Fluorescence Spectroscopy and Elastic–Scattering Spectroscopy," *Phys. Med. Biol.*, 42:803–814, 1997.

Boente et al., "Screening, Images, and Early Diagnosis of Ovarian Cancer," *Clinical Obstetrics and Gynecology*, 37(2):377–391, 1994.

Brunsting and Mullaney, "Differential Light Scattering from Spherical Mammalian Cells," *Biophys. J.*, 14:439–453, 1974.

Dabelsteen et al., "Carbohydrate Changes in Squamous Cell Carcinomas," *APMIS Suppl.* 27, 100:130–138, 1992.

Drezek et al., "Light Scattering from Cells: Finite–Difference Time–Domain Simulations and Goniometric Measurements," *Appl. Opt.*, 38:3651–3661, 1999.

Dunn et al., "Finite–Difference Time–Domain Simulation of Light Scattering from Single Cells," *J. Biomed. Optic.*, 2(3):262–266, 1997.

Gurjar et al., "Imaging human epithelial properties with polarized light–scattering spectroscopy," *Nature Medicine*, 7(11):1245–1248, 2001.

Hung and Lau, "Basic Science of HER–2/neu: a Review," *Semin. Oncol.*, 26(4), Suppl. 12, 51–59, 1999.

Jacques et al., "Imaging Superfacial Tissues with Polarized Light," *Lasers Surg. Med.*, 26:119–129, 2000.

Jacques, "Video imaging with polarized light finds skin cancer margins not visible to dermatologists," as it appears on the web site of the *Oregon Medical Laser Center* (Url: http://omlc.ogi.edu/news/feb98/polarization/index.html), 1998.

Jarry et al., "Coherence and Polarization of Light Propagating Through scattering Media and Biological Tissues,"*Appl. Opt.*, 37:7357–7367, 1998.

Jin et al., "A Histological Morphometric Study of Nuclear Size in Benign and Malignant Neoplasms of the Human Cheek," *Histopathology*, 23:271–274, 1993.

Johnson and Mourant, "Polarized Wavelength–Dependent Measurements of Turbid Media," *Opt. Express*, 4:200–216, 1999.

Kudo et al., "Morphology of Adenocarcinoma in Situ and Microinvasive Adenocarcinoma of the Uterine Cervix. A Cytologic and Ultrastructural Study," *Acta Cytol,*. 35:109–116, 1991.

Kuntz and Saltzman, "Neutrophil Motility in Extracellular Matrix Gels: Mesh Size and Adhesion Affect Speed of Migration," *Biophys. J.*, 72:1472–1480, 1997.

Lam et al., "Detection of Dysplasia and Carcinoma In Situ with a Lung Imaging Fluorescence Endoscope Device," *J of Thoracic & Cardiovascular Surgery*, 105:1035–1040, 1993.

Lam et al., "Localization of Bronchial Intraepithelial Neoplastic Lesions by Fluorescence Bronchoscopy," *Chest*, 113(2):696–702, 1998.

Langer and Vacanti, "Tissue Engineering," *Science*, 260:920–926, 1993.

Meyer and Rustin, "Role of Tumour Markers in Monitoring Epithelial Ovarian Cancer," *Br. J. Cancer*, 82(9):1535–1538, 2000.

Mourant et al., "Mechanism of Light Scattering from Biological Cells Relevant to Noninvasive Optical–Tissue Diagnostics," *Appl. Opt.*, 37:3586–3593, 1998.

Mourant et al., "Predictions and Measurements of Scattering and Absorption Over Broad Wavelength Ranges in Tissue Phantoms," *Appl. Opt.*, 36:949–957, 1997.

Parkhurst and Saltzman, "Quantification of Human Neutrophil Motility in Three–Dimensional Collagen Gels: Effect of Collagen Concentration," *Biophys. J.*, 61:306–315, 1992.

Perelman et al., "Observation of Periodic Fine Structure in Reflectance from Biological Tissue: A New Technique for Measuring Nuclear Size Distribution," *Phys. Rev. Lett.*, 80:627–630, 1998.

Pogue et al., "Multi–wavelength digital colposcopy to aid early detection of cervical cancer," *Biomedical Optical Spectroscopy & Diagnostics/Therapeutic Laser Applications, Tops*, 22(Joint Volume):118–121, 1998.

Riesle et al., "Collagen in Tissue–Engineered Cartilage: Types, Structure, and Crosslinks," *J. Cell. Biochem.*, 71:313–327, 1998.

Sankaran et al., "Polarization Discrimination of Coherently Propagating Light in Turbid Media," *Appl. Opt.*, 38:4252–4261, 1999.

Schmitt and Kumar, "Optical Scattering Properties of Soft Tissue: a Discrete Particle Model," *Appl. Opt.*, 37:2788–2797, 1998.

Schwartz, "Biomarkers and Molecular Epidemiology and Chemoprevention of Oral Carcinogenesis," *Crit. Rev. Oral Biol. Med.*, 11(1):92–112, 2000.

Silverman et al., "Oral leukoplakia and malignant transformation. A follow up study of 257 patients," *Cancer*, 53:563–568, 1984.

Smithpeter et al., "Near Real Time Confocal Microscopy of Cultured Amelanotic Cells: Sources of Signal, Contrast Agents and Limits of Contrast," *J. Biomed. Opt.*, 3(4):429–436, 1998.

Sokolov et al., "Reflectance Spectroscopy with Polarized Light: Is it Sensitive to Cellular and Nuclear Morphology," *Optics Express*, 5(13):302–317, 1999.

Taylor and Schwartz, "Screening for Earlier Ovarian Cancer," *Radiology*, 192:–1–10, 1994.

Trujillo et al., "Method to determine tissue fluorescence efficiency in Vivo and predict signal–to–noise ratio for spectrometers," *Applied Spectroscopy*, 52(7):943–951, 1998.

Utzinger et al., "Performance Estimation of Diagnostic Tests for Cervical Pre–Cancer Based on Fluorescence Spectroscopy: Effects of Tissue Type, Sample Size, Population and Signal to Noise Ratio," *IEEE Trans. Biomed. Eng.*, 46:1293–1303, 1999.

Wheeler et al., "Predictions of Cervical Neoplasia Diagnosis Groups. Discriminant Analysis on Digitized Cell Images," *Analyt. Quant. Cytol. Histol.*, 9(2):169–181, 1987.

Who Collaborating Centre for Oral Pre-cancerous Lesions, "Definitions of leukoplakia and related lesions: an aid to studies on oral pre-cancer," *Oral Surg Oral Med Oral Pathol*, 46(4):518–539, 1978.

* cited by examiner

140
METHODS AND APPARATUS FOR POLARIZED REFLECTANCE SPECTROSCOPY

This application claims priority to provisional patent application Ser. No. 60/192,540 filed Mar. 28, 2000. The entire text of the above-referenced disclosure is specifically incorporated by reference herein without disclaimer.

The government may own rights in the present invention pursuant to grant number CA72650 from the National Institute of Health.

BACKGROUND OF THE INVENTION

1. Field of the Invention

The present invention relates generally to the fields of diagnostic imaging. More particularly, it concerns methods and apparatus for polarized reflectance spectroscopy that may be used to assess cellular and nuclear morphology in order to, for example, diagnose various conditions in various tissues.

2. Description of Related Art

Approximately 1,200,000 people will be diagnosed with cancer in 1999 resulting in approximately 563,000 deaths. The majority of these cancers will be of epithelial origin. Early detection of pre-invasive epithelial neoplasia has the potential to increase patient survival and improve quality of life. However, many of the currently available screening and detection techniques for epithelial pre-cancers do not provide adequate sensitivity and specificity; furthermore, many screening and detection methods require extensive training to yield adequate clinical results. Thus, more sensitive and cost-effective screening and diagnostic techniques are needed to identify curable pre-cancerous lesions.

Pre-cancers are characterized by increased nuclear size, increased nuclear/cytoplasmic ratio, hyperchromasia and pleomorphism, which currently can only be assessed through invasive, painful biopsy. Elastic light scattering spectroscopy may provide a non-invasive tool to assess nuclear morphometry. The wavelength dependence of elastic light scattering is determined by scatterer sizes and refractive indices. Previous work using suspensions of polystyrene spheres and Intralipid with optical properties similar to tissue has shown that the sizes of scattering particles can be estimated from elastic scattering spectra using Mie theory. Recently this principle was applied to estimate distribution of nuclear size in the epithelium of the esophagus. In these experiments, tissue was illuminated with unpolarized light, and the spectrum of reflected light was measured. The reflected light consisted of both singly scattered light originating from the epithelial cells as well as a much stronger multiply scattered component produced in the stroma, which was modulated by hemoglobin absorption. The contributions of the background were modeled and subtracted from the experimental reflectance spectra in order to extract the relatively weak single scattering produced by epithelial cells. Although this approach has demonstrated some utility, its accuracy unfortunately depends strongly on the ability of the model to describe the scattering and absorption properties of the stromal layer.

In view of the above, it would be highly desirable to develop experimental techniques that would allow the elastic light scattering of epithelial cells to be measured directly with less dependence upon modeling capabilities.

SUMMARY OF THE INVENTION

In one respect, the invention is a method for assessing the size of a scattering element of a sample. As used herein, "size" is meant to be read broadly to include, but not to be limited to, size distributions, mean sizes, mean diameters, etc. As used herein, "scattering element" is meant to be read broadly to include any material that causes scattering of radiation. Polarized reflectance spectra of the sample are obtained. A depolarization ratio is calculated using the spectra, and the size of the scattering element is calculated using the depolarization ratio.

In other respects, calculating the size of the scattering element includes varying one or more Mie theory parameters to determine a best fit between the depolarization ratio and a combination of forward and backward scattering terms. The sample may be in vivo. The sample may be in vitro. The sample may include a cell, and the scattering element may include a cytoplasm. The sample may include a cell, and the scattering element may include a cell nucleus. The cell may include a cervical cell. The cell may include an oral mucosa cell.

In another respect, the invention is a method for assessing the refractive index of a scattering element of a sample. Polarized reflectance spectra of the sample are obtained. A depolarization ratio is calculated using the spectra, and the refractive index of the scattering element is calculated using the depolarization ratio.

In another respect, the invention is a method for assessing the size of cell nuclei of a sample. Polarized reflectance spectra of the sample are obtained. A depolarization ratio is calculated using the spectra. One or more Mie theory parameters are varied to determine a best fit between the depolarization ratio and a combination of forward and backward scattering terms, and the size of the cell nuclei is determined using the Mie theory parameters.

In another respect, the invention is a method for assessing the size of a scattering element of a sample. Primary radiation is generated from a source. The primary radiation is polarized to produce polarized primary radiation. The polarized primary radiation is directed to the sample to generate reflected radiation. The reflected radiation is directed through a polarizer to produce filtered reflected radiation. The polarizer is configured to select reflected radiation parallel and perpendicular to the polarization of the polarized primary radiation. The filtered radiation is detected. A depolarization ratio is calculated using the detected filtered radiation, and the size of the scattering element is calculated using the depolarization ratio.

In another respect, the invention is a computer readable media containing program instructions for assessing the size of a scattering element of a sample. The computer readable media includes instructions for calculating a depolarization ratio from polarized reflectance spectra of the sample and instructions for calculating the size of the scattering element using the depolarization ratio.

In another respect, the invention is an apparatus for assessing the size of a scattering element of a sample. The apparatus includes a primary radiation source, a first polarizer, a second polarizer, and a detector. As used herein, "detector" is meant to be read broadly to include associated detector elements such as, but not limited to, filters and the like. The first polarizer is configured to polarize the primary radiation according to a first orientation. The second polarizer is configured to polarize reflected radiation according to a second and third orientation to produce filtered reflected radiation. The second orientation is substantially parallel to the first orientation, and the third orientation is substantially perpendicular to the first orientation. The detector is configured to detect the filtered radiation to produce a polarized reflectance spectra of the sample.

In other respects, the primary radiation source may include a halogen lamp source. The primary radiation source may include a xenon flashlight. The detector may include a plurality of bandpass filters. The detector may include a liquid crystal tunable filter and a variable wave retarder. The detector may include a single grating spectrograph coupled to an intensified photodiode array detector.

In another respect, the invention is a probe for assessing the size of a scattering element of a sample. It includes a tubing, a fiber disc, a plurality of fibers, and a polarizing film. The fiber disc is coupled to the tubing. The plurality of fibers are coupled to the fiber disc, and the fibers include one or more excitation fibers and one or more collection fibers. The polarizing film is divided in at least two parts, a first part in operative relation with the one or more excitation fibers, and a second part in operative relation with the one or more collection fibers.

In other respects, the probe may include one excitation fiber and two collection fibers. The excitation fiber and one of the collection fibers may be in operative relation with the first part of the polarizing film, and the other collection fiber may be in operative relation with the second part of the polarizing film. The first part of the polarizing film may be configured for a parallel polarization orientation and the other part of the polarizing film may be configured for a perpendicular polarization orientation. The probe may also include an optical window configured to protect the polarizing film. The one or more collection fibers may be located symmetrically relative to the one or more excitation fibers. The probe may also include a lens positioned in front of the plurality of fibers; the lens may be configured to create an overlap between an area illuminated by the one or more excitation fibers and areas from which scattering is gathered by the one or more collection fibers.

These features and associated advantages will become apparent with reference to the following detailed description of specific embodiments in connection with the accompanying drawings, wherein like reference numerals have been applied to like elements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
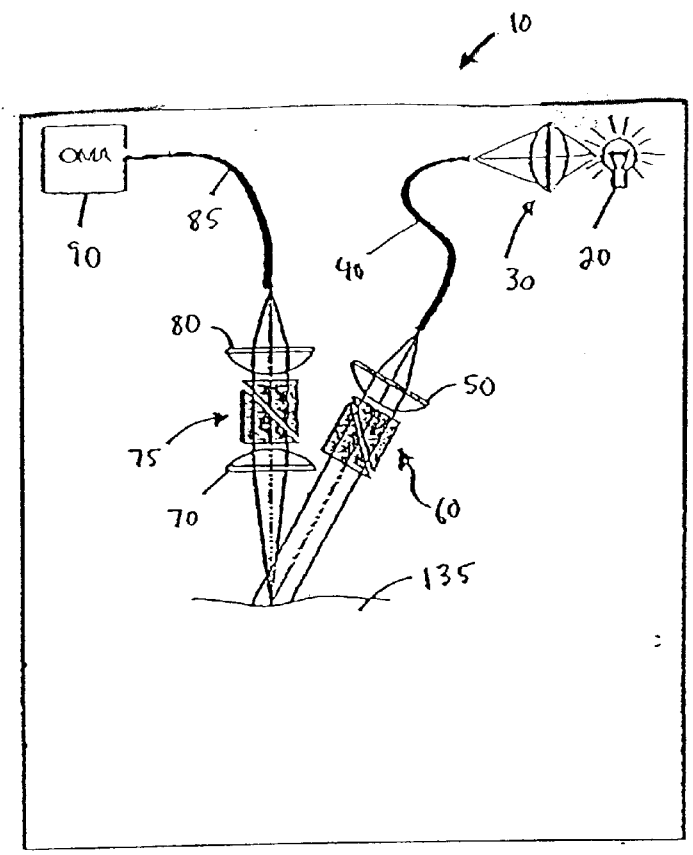
FIG. 1 shows a polarization sensitive spectrometer according to one embodiment of the present disclosure. White light is transported with a fiber optic cable to the specimen site and then polarization filtered with a Glan polarizer. Reflectance is transferred and polarization filtered on to an optical fiber and then spectrally analyzed.

The present disclosure describes apparatus and methods for polarized reflectance spectroscopy that may be used to assess cellular and nuclear morphology in order to diagnose various conditions in various tissues. More particularly, the present disclosure describes methods, systems, computer media, and apparatus for the selective detection of size-dependent scattering characteristics of epithelial cells in vivo and in vitro based on polarized illumination and polarization sensitive detection of scattered light. The techniques described herein advantageously allow for elastic light scattering of tissue, including epithelial cells, to be measured directly with less dependence upon modeling capabilities. Such techniques may be adopted for automated cancer screening and diagnosis of various tissue, including the cervix, without undue reliance upon visualization skills of the operator.

Diagnosis of pre-cancerous and cancerous changes in epithelial tissue such as, but not limited to, the cervix, oral mucosa, esophagus and ovaries are often facilitated with the examination of histologically stained slices of tissue, which are obtained from biopsies. A major indicator is the loss of structural cellular organization and changes in the ratio of nucleus to cytoplasm Techniques described herein are able to detect these changes non-invasively. According to the present disclosure, the mean diameter of the major scattering particles of approximately the first 300 micrometers (or other depths) of tissue surface may be determined. This is the origin of many neoplastic changes, and data obtained by the inventors suggest that the main scattering structures in cells is the nucleus. Thus, methodology disclosed here may be most sensitive to nuclear changes. Not limited to nuclear changes, the principles discussed here may also be used to determine the size distributions of any other scattering particles in any optical turbid media, as will be apparent to those having skill in the art.

When polarized light penetrates deep into a tissue it is multiply scattered and, thus, loses its original polarization. A part of this light returns to the surface producing depolarized multiple scattering and another part is absorbed by hemoglobin giving rise to characteristic valleys at 420, 540 and 580 nm. In contrast, light which undergoes a few scattering events in the upper epithelial layer preserves its polarization. In this disclosure, the wavelength dependence of scattering with polarization parallel and perpendicular to the polarization of the illumination light is explored. To extract size-dependant characteristics of scatterers according to one embodiment, the perpendicular component of scattered light is subtracted from the parallel one. Mie theory calculations are used to describe the observed scattering spectra and to estimate the sizes of the scatterers.

To determine the mean diameter of scattering particles of the first 300 $\mu$m of a tissue, polarized reflectance may be utilized to select backscattered light from about the first 300 $\mu$m of epithelial tissue, and spectral analysis of this light allows a direct determination of the mean scattering particle size without the need for a large dynamic range detector and without the need for intense computational modeling. More specifically, elastic light scattering spectroscopy with polarized illumination/detection dramatically reduces background signals, and resulting spectra can be described as a linear combination of forward and backscattering components determine from Mie theory. Nuclear sizes and refractive indices may be extracted by fitting experimental spectra to this model. Because reflectance spectroscopy as described herein provides valuable information regarding scattering characteristics of a sample, it may be used to obtained quantitative morphological information, which may be used for non-invasive detection of, for instance, neoplastic changes.

Selecting backscattered light from shallow regions of tissue is made possible, in part, because light originating in the uppermost tissue layer has been found to be backscattered with a minimal amount of scattering events and therefore maintains its polarization. It has been found that, under certain conditions, this light is about 5% of the total reflected light. When a tissue is illuminated with polarized light, it has been found that subtracting the difference in the parallel polarized filtered image and the perpendicular polarized filtered image removes about 90% of light originating from deeper tissue layers. It has been found that normalization by an image—dividing the difference in parallel/perpendicular filtered images by the sum of the parallel/perpendicular filtered images—cancels common attenuation. It has also been found that specular reflected light may be reduced, or eliminated by using a detector slightly tilted with respect to the surface of tissue (or other optical media) under study.

For at least three different reasons, polarized reflectance spectroscopy disclosed herein allows for the assessment of scattering properties of tissue including, but not limited to, the epithelial layer (this assessment, in turn, allows for the identification of various conditions such as those associated with neoplastic changes). First the usage of polarized reflectance eliminates the need of complex modeling of tissue scattering and absorption to extract a signal which would be as low as 1% of the total reflectance. Second, a signal obtained within the first 300 micrometers of the tissue surface is simpler to model and optical parameters such as absorption can be extracted with less computational efforts. Third, fine periodic structures are enhanced by orders of magnitude and mean nuclear size can be obtained with good accuracy.

FIG. 1 shows an optical setup of an apparatus according to one embodiment of the present disclosure. This apparatus may be used for measuring on a single spot. Apparatus 10 of FIG. 1 includes a primary radiation source 20, coupling lens 30, a fiber 40, lens 50, polarizer 60, sample 135, lens 70, polarizer 75, lens 80, fiber 85, and optical multi channel analyzer 90. Those having skill in the art will recognize that FIG. 1 is simply a schematic diagram and will note that other optical elements, as is known in the art, may be utilized as needed to, for instance, direct radiation. Additionally, it will be understood that "lens" as used herein may refer to various optical elements suitable for controllably directing radiation from one location to another. Likewise, the term "polarizer" is meant to be read broadly to encompass any device suitable for providing polarized radiation. In operation, radiation from source 20 (which may be a halogen source, a xenon flashlight, a pulsed source, or any other source suitable for reflectance spectroscopy as is known in the art) is transported via cable 40, polarization filtered via polarizer 60 (which may be Glan polarizer or any other polarizer known in the art), and delivered to sample 135. Reflectance is transferred and polarization filtered via polarizer 75, delivered to cable 85, and spectrally analyzed via analyzer 90 (or via any other detector suitable for reflectance spectroscopy, as is known in the art).

In one embodiment, the polarization sensitive spectrometer in FIG. 1 measures reflectance at a single spot with a diameter of approximately 600 micrometer. This instrument allows the investigation of scattering properties of tissue phantoms, cell cultures and in-vitro and in-vivo specimens. As described more fully above, the system, in one embodiment, includes a polarization filtered white light source and a polarization filtered detection system with an optical multi channel analyzer. Such an apparatus may be used to predict scattering characteristics (including the assessment of the size of scattering elements) of a layer of defined structures on top of a diffusely scattering background, similar to, for example, epithelial lined tissue.

Figure 2:
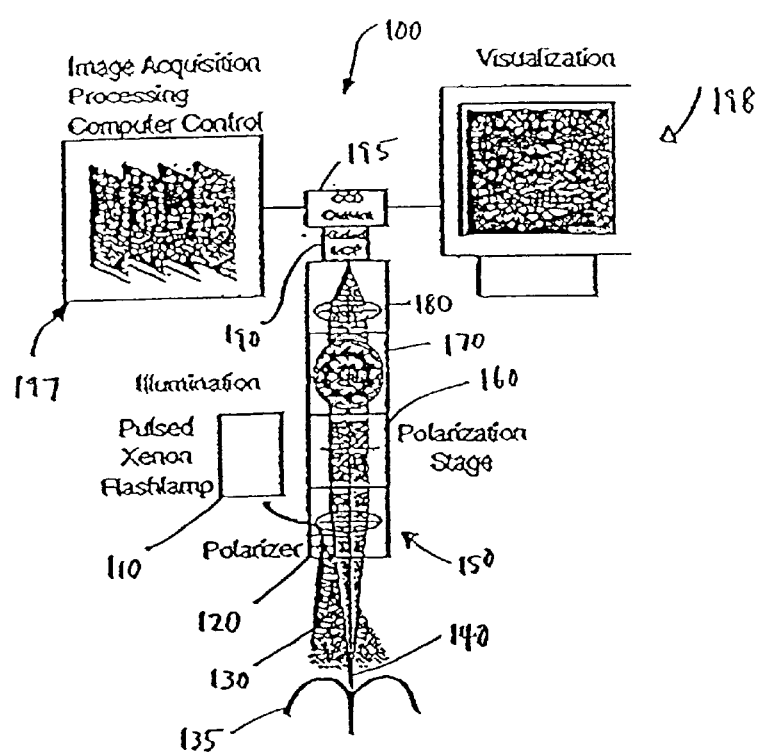
FIG. 2 shows an apparatus for reflectance imaging according to one embodiment of the present disclosure. This apparatus may be used to analyze various tissue, including the cervix. Light from a pulsed Xenon light source is linearly polarized and illuminated on to the cervix. Reflected light is collimated and passes a parallel and vertical polarization filter. Wavelength is selected with either a tunable filter or mechanical filter wheel. Gated detection is made possible with an intensified CCD camera.

FIG. 2 shows an apparatus according to one embodiment suitable for sample imaging. Apparatus 100 of FIG. 2 includes primary radiation source 110, polarizer, primary radiation 130, sample 135, reflected radiation 140, optics 150, polarizer 160, filter 170, lens 180, gated microchannel plate 190, camera 195, analysis unit 197, and display 198. In operation, light from source 110 (which, in one embodiment may be a pulsed Xenon light source) is linearly polarized and illuminated onto sample 135 (which, in one embodiment may be a cervix). Reflected light is collimated and passes a parallel and vertical polarization filter shown as polarizer 160. Wavelength is selected with either a tunable filter or mechanical filter wheel shown as filter 170. Gated detection is made possible with an intensified CCD camera shown as camera 195.

If a xenon flashlight source 110 is used, the flashlight produces incoherent and randomly disorganized light. In one embodiment, polarizer 120 selects linear polarized illumination light (50% transmission). A polarization filter with the same characteristics and one with perpendicular characteristics (polarizer 160) is mounted in a mechanical filter wheel in front of the imaging camera, camera 195. A second filter wheel (filter 170) contains bandpass filters to obtain spectrally resolved reflectance images. If more than 10 wavelengths need to be measured, a liquid-crystal tunable filter or the like may be used instead of the second filter wheel. However, because such tunable filters are based on polarization techniques, cross-polarized light detection requires a variable wave retarder in front of the tunable filter (not shown). This retarder must be variable because the degree of retardation depends on the investigated wavelength. Intensified camera, camera 195, measures the reflectance images.

Figure 3:
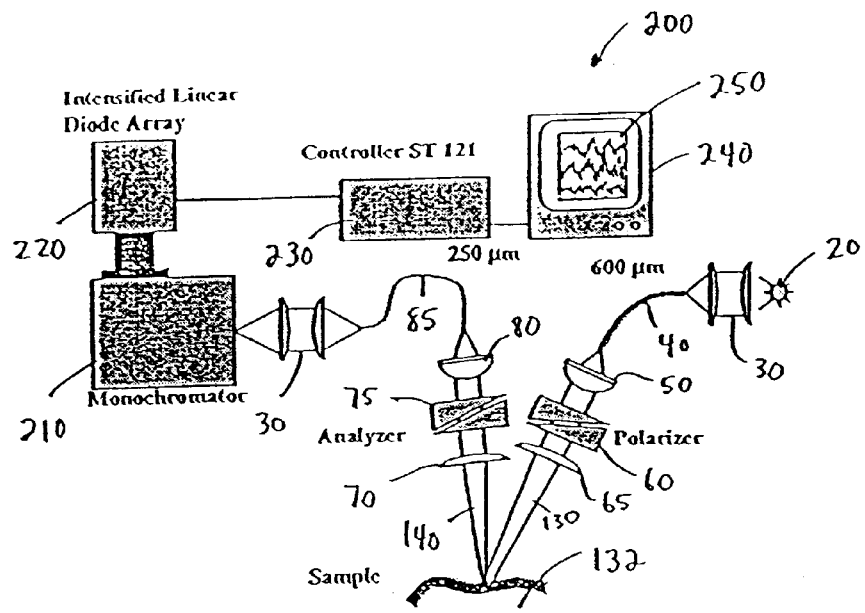
FIG. 3 is a diagram of spectrometer used for reflectance measurements with polarized illumination/detection according to one embodiment of the present disclosure.

FIG. 3 shows a block diagram of a reflectance spectrometer with polarized illumination/detection according to one embodiment. Apparatus 200 of FIG. 3 includes primary radiation source 20, coupling lens 30, fiber 40, lens 50, polarizer 60, lens 65, primary radiation 130, sample 132, reflected radiation 140, lens 70, polarizer 75, lens 80, fiber 85, lens 30, monochromator 210, diode array 220, controller 230, and display 240, showing spectra data 250.

In one embodiment, apparatus 200 was setup as follows. Excitation light from a halogen lamp source (which is commercially available from Dolan-Jenner Industries) is coupled into a 600 $\mu$m core diameter fused silica optical fiber (NA 0.22, commercially available from Fiberguide Industries). The light delivered by the fiber is collimated, passes through a linear polarizer, and is focused on a sample by a lens with focal distance f=60 mm. The scattered light is collected and coupled into a 250 $\mu$m core diameter fused silica optical fiber (NA 0.22, commercially available from Fiberguide Industries) using two lenses with f=40 mm and f=16 mm, respectively. A linear polarizer-analyzer is placed between the two lenses to measure the scattered light with polarization perpendicular or parallel to the polarization of the illumination light. The collected signal is focused on the 250 $\mu$m entrance slit of a single grating spectrograph (f/3.8, 300 lines/mm grating, Monospec 18, available commercially from Jarrel Ash) coupled to an intensified photodiode array detector (IRY-700, commercially available from Princeton Instruments). A PC computer controls data acquisition. All lenses used in the set-up are plano-convex fused silica lenses. A mercury lamp (ORIEL) is used to provide a wavelength calibration for the spectrometer. The system's spectral resolution is measured from the width of He-Ne 543.5 nm and 632.8 nm lasers and was found to be ca. 5 nm. A constant angle of 36° was maintained between the excitation and collection arms. The light was collected from the middle of the illuminated spot on the sample. The polarization of the excitation light was perpendicular to the plane formed by the excitation and the collection arms. In other words the illumination light was perpendicular to the scattering plane. Collection times and powers used are summarized below in Table 1, as part of Example 1.

EXAMPLE 1

The following non-limiting example is included to demonstrate a specific embodiment of the invention. It should be appreciated by those of skill in the art that the techniques disclosed in the example which follow represent techniques discovered by the inventors to function well in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the invention.

The inventors measured light scattering spectra from samples of progressively increasing complexity designed to mimic squamous epithelial tissue, which includes multiple layers of epithelial cells atop a network of stromal collagen. The inventors began by placing either polystyrene spheres or squamous epithelial cells atop a strongly scattering substrate and progressed to cervical biopsies, and finally to in vivo oral mucosa. Polystyrene beads (5 $\mu$m and 10 $\mu$m diameter) were purchased from Bangs Laboratories. SiHa cells (cervical epithelial cancer cells) were provided by the University of Texas M.D. Anderson Cancer Center.

Suspensions of 5 $\mu$m beads in water or glycerol and 10 $\mu$m beads in glycerol (100–200 $\mu$l) were placed atop a diffusely scattering substrate (SRS-99, Labsphere). The substrate strongly depolarizes polarized excitation light and mimics the multiple scattering produced in the stromal layer of epithelial tissue. Glycerol was used to decrease the relative refractive index of the beads from about 1.2 (water) to 1.08 (glycerol) and to provide a viscous environment which prevented the beads from settling during the course of the experiment. The concentration of 5 $\mu$m polystyrene beads was chosen so that the beads would approximately form a monolayer if they all settled down on the surface of the substrate. The same concentration (beads per ml of solution) was used in experiments with 10 $\mu$m spheres. To prevent beads from aggregating, 3 mg/ml of bovine serum albumin (BSA) were added to the water solution.

A monolayer of 5 $\mu$m beads was also formed atop the same diffusely scattering substrate. To prepare the monolayer, the stock solution of 5 $\mu$m beads (10%, w/w) was first diluted in ethanol by a factor of ca. 40. Then a 50 $\mu$l drop of the suspension was placed directly on the surface of the substrate and was allowed to dry. Capillary forces play the major role in formation of the monolayer. This technique produces large areas of highly packed uniformly distributed polystyrene spheres. The quality of prepared monolayers was monitored using a light microscope (Olympus) in reflectance. To measure reflectance spectra in a liquid environment a drop of water was gently added on the top of the monolayer.

Next, cervical epithelial cells were used in place of polystyrene beads. A cell has two distinct interfaces that scatter light: a cytoplasmic membrane and a nuclear membrane. Two approaches were used to characterize the scattering associated with nuclei. First, a high concentration of bovine serum albumin (BSA) was used to match the refractive index of the cytoplasm with the refractive index of the surrounding medium. This effectively eliminates the cytoplasm as an optical interface and allows the scattering of nuclei to be directly assessed. Next, acetic acid (AA) was added to a cell suspension to selectively enhance scattering of nuclei. SiHa cells (cervical epithelial cancer cells) were received in culture medium and were first washed three times in PBS buffer. Then they were divided into three equal aliquots. Cells in each aliquot were allowed to settle and were resuspended in three different solutions: a pure isotonic PBS buffer, a 20% (g per 100 ml) BSA in PBS, and a 3% (v/v) acetic acid in PBS.

Four frozen normal cervical biopsies were obtained from Cooperative Human Tissue Network (CHTN). Biopsies were thawed in PBS buffer for about 5–15 minutes immediately before the reflectance measurements. PBS buffer was periodically added to the samples to keep them from drying during the course of experiments.

A normal volunteer was recruited at the University of Texas at Austin for in vivo reflectance measurements of oral cavity mucosa.

Reflectance measurements were made from samples consisting of suspensions of scatterers atop the multiply scattering substrate. For each sample, scattered light was measured with polarization parallel and perpendicular to the polarization of the illumination light. Dark current was recorded and subtracted from all measured spectra. Then the depolarization ratio (D) was calculated (Equation 1):

$$D(\lambda) = \frac{I_{||}(\lambda) - I_{\perp}(\lambda)}{I_{||}(\lambda) + I_{\perp}(\lambda)} \quad (1)$$

where $I_{||}(\lambda)$ is the component of the scattered light with polarization parallel to the incident light and $I_{\perp}(\lambda)$ is the component with polarization perpendicular to the incident light and $\lambda$ is the wavelength of the incident light.

Reflectance measurements were also made from the biopsy and the in vivo oral mucosa. The depolarization ratio can not be directly used to assess the scattering characteristics of the epithelial layer in the cervical biopsies and in the in vivo measurements because both the parallel and the perpendicular components of the reflectance spectrum have strong contributions from hemoglobin absorption that dominate the depolarization ratio spectrum. Instead the perpendicular component of light scattered by cervical or oral epithelium was first subtracted from the parallel component and the result was normalized to the total intensity of light (the perpendicular plus the parallel components) collected from a diffuse scattering substrate alone. The normalization accounts for spectral characteristics of the excitation lamp and the spectrometer.

Figure 4:
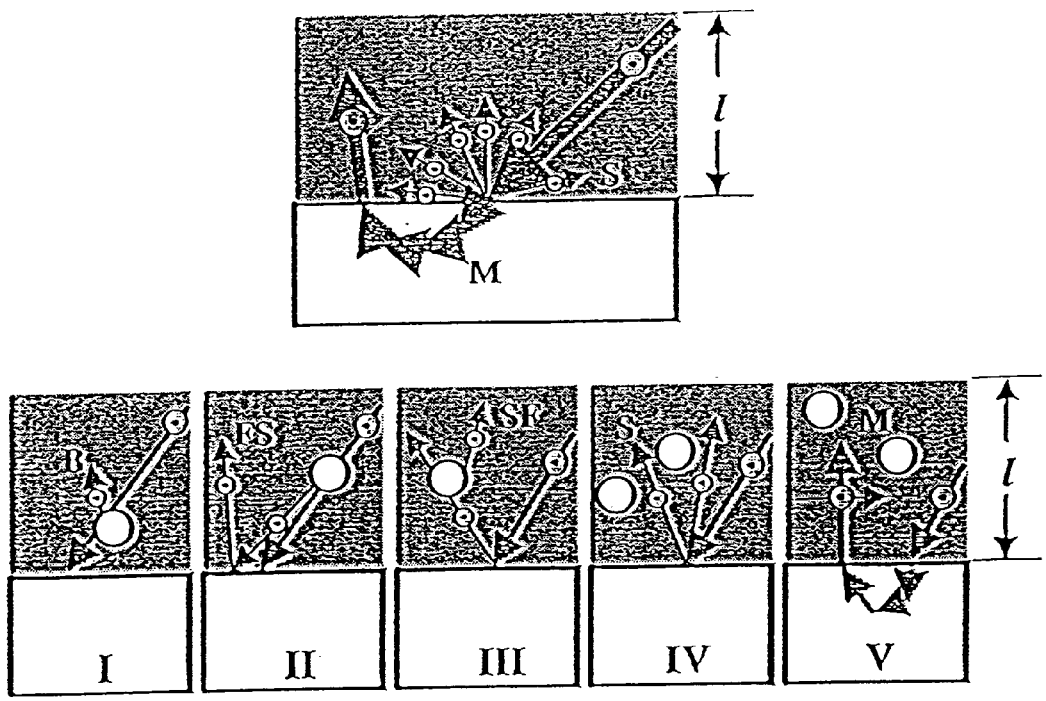
FIG. 4 is a schematic presentation of polarized light scattering from diffusely scattering substrate alone (top) and from spherical scatterers placed atop the substrate (bottom). Five different types of scattering events (I–V) can take place and are described in the text.

To understand the behavior of scatterers placed atop a diffusely scattering substrate, it is useful to describe the scattering properties of the substrate alone. The inventors' data show that for the substrate alone, the intensity of light scattered with polarization parallel to the polarization of the illumination light is about 6% higher than that with polarization in the perpendicular direction. Thus, although most of the light is depolarized after scattering from the substrate surface, a small portion of light undergoes single scattering events and preserves the original polarization (FIG. 4, left). Thus, the scattering from the substrate alone can be described by equations (2 and 3):

$$I_{||S}(\lambda) = I_0(\lambda)S(\lambda)\frac{\Delta\theta}{2\pi} + \frac{1}{2}I_0(\lambda)M(\lambda)\frac{\Delta\theta}{2\pi} \quad (2)$$

-continued $$I_{\perp S}(\lambda) = \frac{1}{2} I_0(\lambda) M(\lambda) \frac{\Delta\theta}{2\pi} \quad (3)$$

Here $I_0(\lambda)$ is the intensity of the illumination light, $I_{\parallel S}(\lambda)$ and $I_{\perp S}(\lambda)$ are the light scattered by the substrate with polarization parallel and perpendicular to the polarization of the illumination light, $S(\lambda)$ and $M(\lambda)$ are the probabilities of light undergoing single and multiple scattering, respectively, and $\Delta\theta$ is the collection solid angle of our experimental setup. The inventors assume that light is scattered isotropically in the substrate. Since all light undergoes scattering, the sum of $S(\lambda)+M(\lambda)$ must be one:

$$S(\lambda)+M(\lambda)=1 \quad (4)$$

When a suspension of scatterers of thickness l is introduced atop the diffusely scattering substrate a number of scattering processes can occur (FIG. 4, bottom). The illumination beam is backscattered and forward scattered as it travels through the suspension of scatterers, preserving its polarization (FIG. 4, I and II). The forward scattered light and the portion of the illumination light that does not undergo any scattering events reach the substrate where they undergo single and multiple scattering. The singly scattered light can undergo single forward scattering events as it travels back through the suspension of scatterers (FIG. 4, III) or reach a detector without undergoing additional scattering events (FIG. 4, IV). This portion of the light is still polarized in the same direction as the polarization of the illumination light. The inventors assume that only single scattering events are likely in a suspension of scattering particles. This is a reasonable assumption, considering that in the inventors' experiments the total amount of scatterers in a suspension corresponds to one monolayer coverage in the case of polystyrene beads and a few monolayers in the case of cervical cells. Subsequent scattering events of the multiply scattered light do not change its randomized polarization (FIG. 4, V). Taking into account the above assumptions, the scattered light which preserves the original polarization, $I_{\parallel B}$, can be written as equation (5) where each of the five terms represents the type of scattering depicted in the same order as in FIG. 4:

$$I_{\parallel B}(\lambda) = I_0(\lambda)B(\lambda)Cl + \frac{\Delta\theta}{2\pi} I_0(\lambda)F(\lambda)S(\lambda)Cl(1 - Cl\sigma(\lambda)) + \quad (5)$$
$$\frac{\Delta\theta}{2\pi} I_0(\lambda)S(\lambda)F(\lambda)Cl(1 - Cl\sigma(\lambda)) +$$
$$\frac{\Delta\theta}{2\pi} I_0(\lambda)S(\lambda)(1 - Cl\sigma(\lambda)) + \frac{1}{2} I_0(\lambda)M(\lambda)\frac{\Delta\theta}{2\pi}(1 - Cl\sigma(\lambda))$$

$$F(\lambda) = \int_{\Delta\theta f} P(\lambda, \theta)\sin\theta d\theta \quad (6)$$

$$B(\lambda) = \int_{\Delta\theta b} P(\lambda, \theta)\sin\theta d\theta \quad (7)$$

where $B(\lambda)$ and $F(\lambda)$ are the wavelength dependent cross-sections for backward and forward scattering of light by a single scattering particle, respectively obtained by integrating the angular dependent scattering cross-section $P(\lambda,\theta)$ (equations 6 and 7). The backscattering cross-section $B(\lambda)$ is calculated for the range of collection angles $\Delta\theta b=139°–149°$ degree and the forward scattering cross-section $F(\lambda)$ is calculated over $\Delta\theta f=(-5°)-(5°)$. The term $\sigma(\lambda)$ is the total scattering cross-section for a single scattering particle, and C is the number of scatterers per unit volume. Similarly, the scattered light polarized orthogonal to the illumination polarization, $I_{\perp B}(\lambda)$, can be described as equation (8):

$$I_{\perp B}(\lambda) = \frac{1}{2} I_0(\lambda) M(\lambda) \frac{\Delta\theta}{2\pi}(1 - Cl\sigma(\lambda)) \quad (8)$$

Thus, the depolarization ratio is given by equation (9). The inventors take into account only terms linear in $F(\lambda)$, $B(\lambda)$ and $\sigma(\lambda)$ because it is assumed that only single scattering events occur in the top layer:

$$\frac{I_{\parallel B}(\lambda) - I_{\perp B}(\lambda)}{I_{\parallel B}(\lambda) + I_{\perp B}(\lambda)} = \quad (9)$$

$$\frac{\frac{2\pi Cl}{\Delta\theta} B(\lambda) + ClS(\lambda)F(\lambda) + ClS(\lambda)[F(\lambda) - \sigma(\lambda)] + S(\lambda)}{1 + \frac{2\pi Cl}{\Delta\theta} B(\lambda) + Cl[2S(\lambda)F(\lambda) - \sigma(\lambda)]}$$

The scattering cross-sections of individual particles are much smaller than 1 and in these experiments the concentrations and pathlengths were small. Even for polystyrene beads in water, with the largest relative index $(n_{rel}=1.2)$ of all samples studied, the inventors can approximate:

$$1 + \frac{2\pi Cl}{\Delta\theta} B(\lambda) + Cl[2S(\lambda)F(\lambda) - \sigma(\lambda)] \approx 1 \quad (10)$$

Thus, the depolarization ratio can be rewritten as:

$$\frac{I_{\parallel B}(\lambda) - I_{\perp B}(\lambda)}{I_{\parallel B}(\lambda) + I_{\perp B}(\lambda)} \approx \quad (11)$$

$$\frac{2\pi Cl}{\Delta\theta} B(\lambda) + ClS(\lambda)F(\lambda) + ClS(\lambda)[F(\lambda) - \sigma(\lambda)] + S(\lambda)$$

All the scatterers studied here were highly forward scattering, where $F \approx \sigma$, so $F-\sigma \approx 0$. The inventors' data also show that the term $SS(\lambda)$ does not strongly depend on wavelength and can be approximated by a constant. Taking this into account, the inventors obtain equation (12) for the depolarization ratio of scatterers on atop a diffusely scattering substrate:

$$\frac{I_{\parallel B}(\lambda) - I_{\perp B}(\lambda)}{I_{\parallel B}(\lambda) + I_{\perp B}(\lambda)} \approx \frac{2\pi Cl}{\Delta\theta} B(\lambda) + ClS(\lambda)F(\lambda) + S(\lambda) \quad (12)$$
$$= k_1 B(\lambda) + k_2 F(\lambda) + DC$$

which is a linear combination of a forward scattering term, a backward scattering term and a DC offset where $F(\lambda)$ and $B(\lambda)$ are defined in equations (6) and (7).

Experimental depolarization ratio spectra were fit to a linear combination of forward and backward scattering terms and a DC offset. Mie theory calculations were used to compute the forward and backward theoretical scattering spectra in the spectral range exploited in these studies. To account for the optical system's finite spectral resolution, computed curves (scattered intensity vs. wavelength) were convolved with a Gaussian of width equivalent to the system's resolution (FWHM=5 nm). Experimental data were then fit to equation (12) using a standard non-negative least squares algorithm to calculate coefficients for forward scattering and backscattering, in addition to a DC offset. The best fits were selected as those with the smallest value of the standard sum of the squared error (SSE). For all fits the $\chi^2$ factors (the goodness of the fits) were calculated. The $\chi^2$ factors indicated that there was at least a 99% chance that the errors were due to random fluctuations.

Mie theory calculations were implemented using MAT-LAB to provide additional flexibility over commercially available Mie software. MATLAB code was verified by comparing results to tabulated curves known in the art (See, e.g., H. van de Hulst. Light Scattering by Small Particles. (Dover, New York, N.Y. 1957). For each wavelength, calculations were performed either for a single-sized particle or a Gaussian distribution of particle sizes as noted. Cellular constituents were assumed to be non-dispersive.

for the nucleus. In this case the refractive index of the surrounding medium corresponds to the refractive index of the cytoplasm. Then, the refractive indices which resulted in the best fit were directly applied to fit the depolarization ratio spectrum of cells in PBS changing only the DC offset and coefficients for forward and backscattering components of both the nucleus and the cytoplasm. The best fit for cells in AA solution was obtained independently varying refractive index of the nucleus from 1.43 to 1.45.

Biopsies and In Vivo Measurements. Refractive indices for the cytoplasm and nucleus derived from the experiments with cells in BSA and PBS solutions were used to fit the depolarization ratio spectra of cervical biopsies and in vivo

TABLE 1 below summarizes the fitting procedures used for different samples.

| Sample | Collection Parameters (time/power) | Mie Theory Calculations | |
|---|---|---|---|
| | | Fixed Parameters | Parameters Varied* |
| Polystyrene Beads (water/glycerol) | 40–80 sec/370 $\mu$W | Diameters of beads, refractive indices of beads and solutions (water and glycerol) | Only $k_1$, $k_2$ and DC |
| Cells in BSA | 300 sec/370 $\mu$W | Mean diameter and distribution of nuclear sizes | Refractive indices of the nuclei and the surrounding medium (cytoplasm); $k_1$, $k_2$ and DC for nuclei |
| Cells in PBS | 300 sec/370 $\mu$W | Mean diameters and distributions of nuclear and cytoplasm sizes; refractive indices of nuclei, cytoplasm and the medium (water) | $k_1$, $k_2$ and DC for both the nuclei and the cytoplasm |
| Cells in AA | 300 sec/370 $\mu$W | Mean diameter and distribution of nuclear sizes; refractive index of the medium (cytoplasm) | Refractive index of nuclei; $k_1$, $k_2$ and DC for nuclei. |
| Cervical Biopsies | 200 sec/370 $\mu$W | Refractive indices of nuclei and cytoplasm | Mean diameters of nuclei and cytoplasm; $k_1$, $k_2$ and DC for both the nuclei and the cytoplasm |
| In vivo oral mucosa | 60 sec/370 $\mu$W | Refractive indices of nuclei and the medium (cytoplasm) | Mean diameter of nuclei; $k_1$, $k_2$ and DC for nuclei |

*Coefficients for backward ($k_1$), forward ($k_2$) Mie scattering components and DC offset were always varied to achieve the best fits.

Cells. In the case of cells in BSA and AA it was assumed that nuclei are the main scatterers and are suspended in a medium with refractive index of cytoplasm. In pure PBS buffer, a cell was treated as consisting of two independent scatterers: a nucleus in an environment with refractive index of cytoplasm and a cytoplasm in an environment with refractive index of water. Thus, depolarization ratio spectra of cells in BSA and AA solutions were fit to a linear combination of three components: forward and backward Mie scattering curves of a nucleus and a DC offset. For cells in PBS solution five components were used: forward and backward Mie scattering terms for both the nucleus and the cytoplasm plus a DC offset.

Mean diameters of cells and nuclei were estimated using phase-contrast microscopy. A Gaussian distribution of diameters was used in the fitting process, Mie theory was used to calculate B($\lambda$) and F($\lambda$) for the measured size distributions at varying refractive indices. For each combination of Mie theory parameters, a separate least squares fit yielded the coefficients $k_1$, $k_2$, DC and the standard sum of the squared error (SSE). The best fit was selected as that with the smallest SSE. First, the best fit was obtained for the depolarization ratio spectrum of cells in BSA. To achieve the best fit, the refractive indices were varied in the range from 1.36 to 1.38 for the surrounding medium and from 1.39 to 1.43 measurements. Here, the mean diameters of the scatterers were varied to achieve the best fits. A Gaussian distribution of sizes was used in Mie theory calculations. A standard deviation ($\Delta$) of nucleus size distribution $\Delta \cong 1$ $\mu$m was previously reported in morphometric studies which included two normal sites from cervical epithelium. In a study of cervical epithelial sites with moderate dysplasia (10 cases studied) it was demonstrated that the standard deviation could vary from about 1 $\mu$m up to ca 4 $\mu$m. However, it is known that the deviation of nuclear sizes increases in dysplasia. Thus, in the present studies of normal cervical biopsies and normal oral cavity in vivo the inventors limited their analysis to distributions with only two standard deviation values $\Delta=1$ $\mu$m and 2 $\mu$m to simplify Mie theory calculations.

Figures 5A, 5B, 5C:
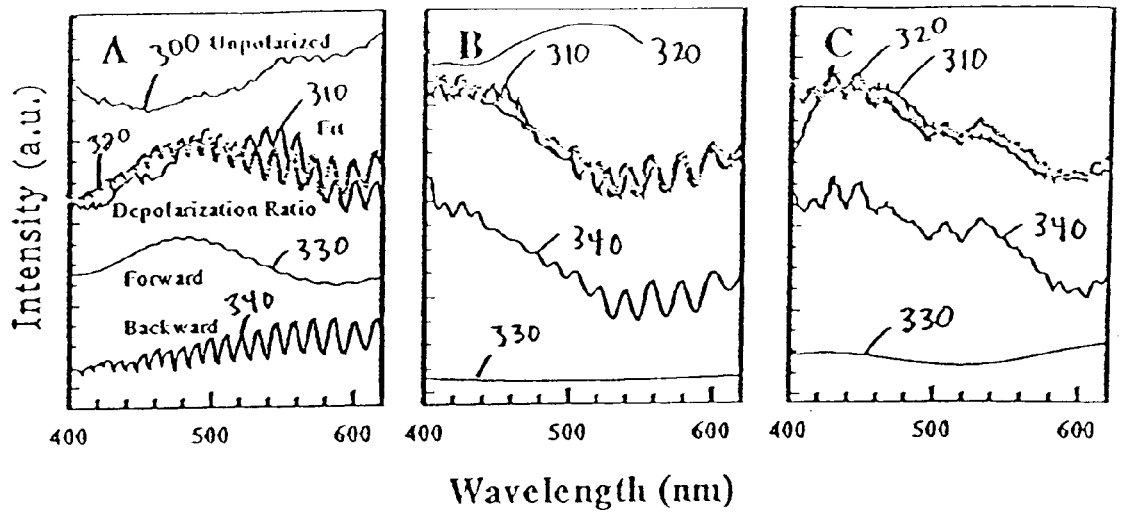
FIGS. 5A–5C are plots showing reflectance spectra and forward and backward scattering spectra calculated from Mie theory for: 5 $\mu$m polystyrene beads in water (A); 5 $\mu$m polystyrene beads in glycerol (B); and 10 $\mu$m polystyrene beads in glycerol (C). Reflectance spectrum obtained using unpolarized detection is shown as 300; depolarization ratio spectra as 310; fits to equation (12) as line 320; forward components of Mie scattering as line 330; backscattering Mie components as line 340. The theoretical curves are multiplied by coefficients extracted from the least-square algorithm used to achieve the best fits for the experimental data. Arbitrary DC offsets are added to theoretical curves in order to facilitate comparison of all curves on one graph.

FIGS. 5A–5C (see Brief Description of the Drawings) shows the experimental elastic scattering spectra and forward and backward scattering spectra calculated from Mie theory for 5 $\mu$m polystyrene beads in water and glycerol and 10 $\mu$m beads in glycerol.

First, the inventors compared the spectrum obtained using unpolarized illumination/detection with the depolarization ratio spectrum for 5 $\mu$m beads in water (FIG. 5A, lines 300 and 310, respectively). The spectrum obtained with unpolarized light is dominated by a diffuse background due to multiply scattered light. The depolarization ratios however do show features predicted by Mie theory for 5 μm beads in water as well as for 5 μm and 10 μm beads in glycerol (FIGS. 5A–5C, curves 310). The depolarization ratio spectra can be adequately described using a linear combination (FIGS. 5A–5C, curves 320) of forward (FIGS. 5A–5C, curves 330) and backward scattering (FIG. 5, curves 340) components calculated based on Mie theory.

Figures 6A, 6B:
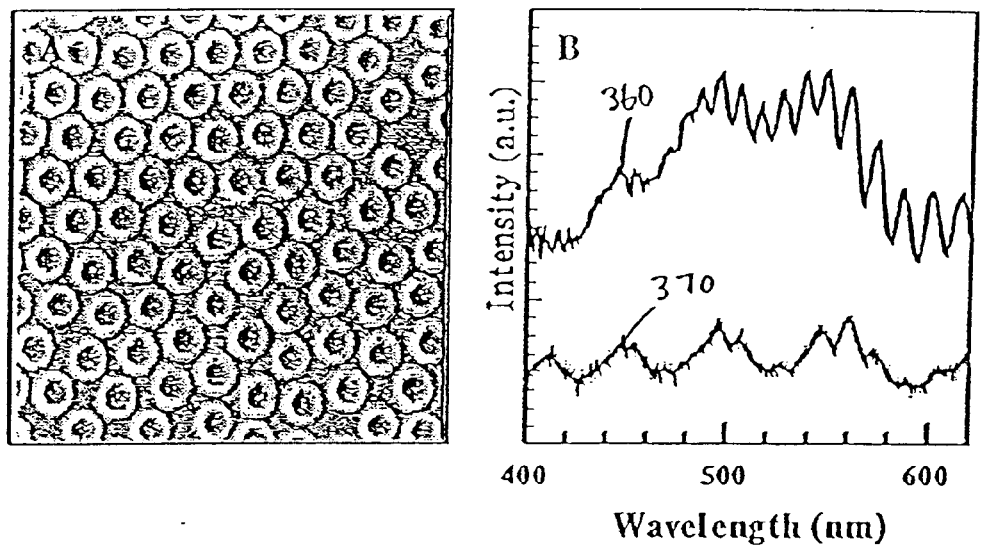
FIGS. 6A and 6B are plots showing density dependence of scattering of 5 $\mu$m polystyrene beads in water: (A) a semi-regular monolayer of 5 $\mu$m polystyrene beads; (B) depolarization ratio spectra of a water suspension (as line 360) and of a monolayer of the beads (as line 370).

When 5 μm polystyrene beads were self-assembled in a semi-regular monolayer on the surface of the substrate a new periodic component was observed (see FIG. 6, see also Brief Description of the Drawings). This periodicity is not described by Mie theory for isolated 5 μm beads in water. It is believed that the observed periodicity most likely originates from the light scattered in the gaps between the closely spaced polystyrene beads and thus could be related to arrangement of the scatterers in the monolayer.

Figures 7A, 7B, 7C, 7D, 7E:
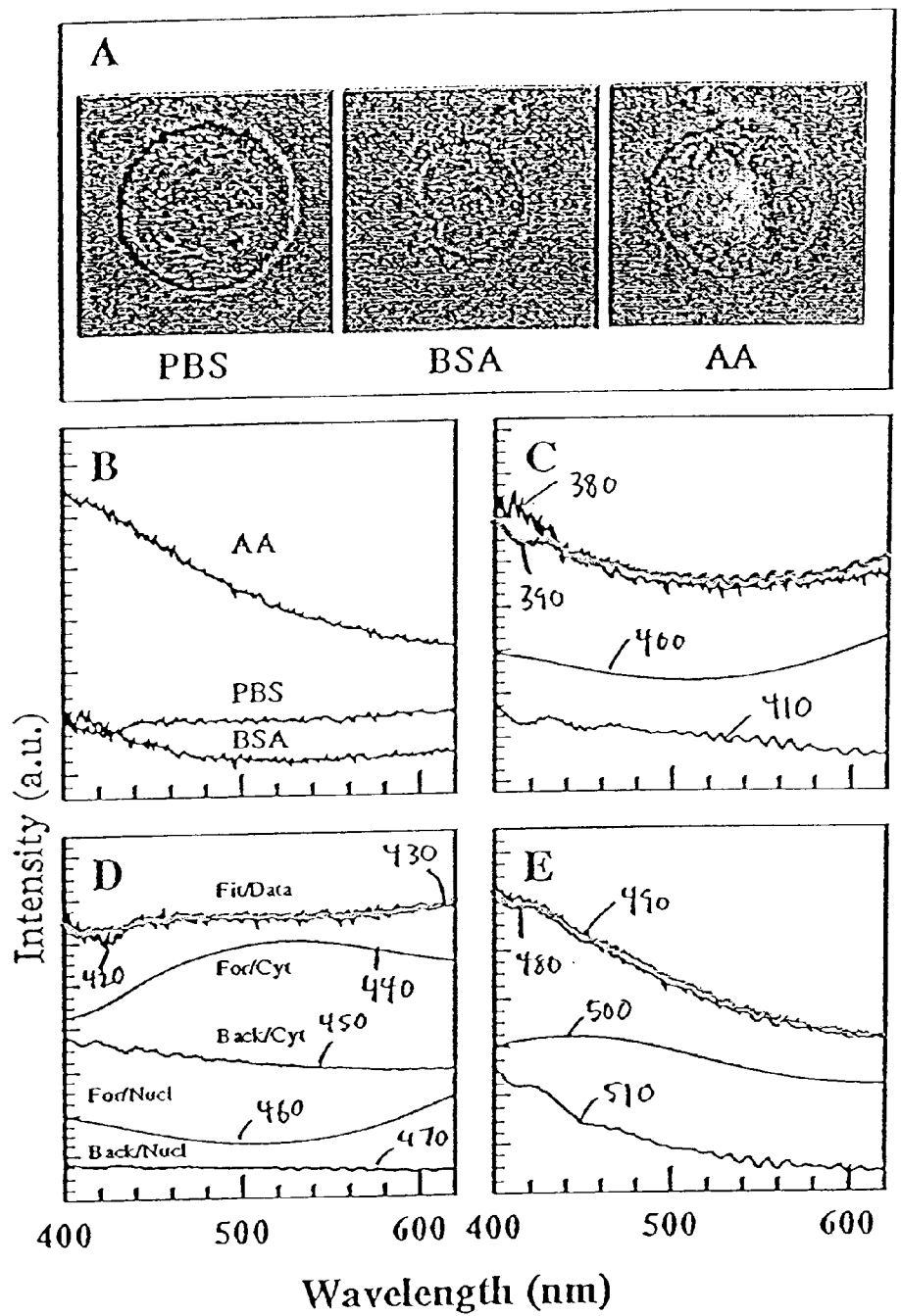
FIGS. 7A–7E are photos and plots showing scattering spectra of SiHa cells: (A) phase-contrast photographs of cells in: a pure PBS buffer (left), BSA/PBS solution that matches the refractive index of the cytoplasm (middle), and acetic acid/PBS solution (right); (B) reflectance spectra of SiHa cells in the presence of acetic acid (AA), in the PBS buffer (PBS), and in the presence of high concentration of BSA (BSA). Experimentally measured depolarization ratio spectra and Mie theory calculations for scattering of: (C) cells in BSA/PBS (measured depolarization ratio spectrum—line 380, the best fit to equation (12)—line 390, forward Mie scattering component of the nucleus —line 400, backscattering of the nucleus—line 410); (D) cells in PBS (measured depolarization ratio spectrum—line 420, the best fit to equation (12)—line 430, forward Mie scattering component of the cytoplasm—line 440, backscattering of the cytoplasm—line 450, forward Mie scattering component of the nucleus—line 460, backscattering of the nucleus—line 470); (E) cells in acetic acid/PBS (measured depolarization ratio spectrum—line 490, the best fit to equation (12)—line 480, forward Mie scattering component of the nucleus—line 500, backscattering of the nucleus—line 510). The theoretical curves are multiplied by coefficients extracted from the least-square algorithm used to achieve the best fits for the experimental data. Arbitrary DC offsets are added to theoretical curves in order to facilitate comparison within one plot.

FIG. 7A (see Brief Description of the Drawings) shows phase-contrast microscopic photographs of cells in different solvents. In PBS, both the cytoplasmic membrane and the nucleus can be clearly seen. In BSA, the cytoplasmic membrane is practically invisible and the contrast of the nuclear membrane is enhanced. After addition of AA (acetic acid), the nucleus decreases in size, probably due to partial dehydration and appears to be much brighter than the surrounding medium, indicating an increase in relative refractive index. Depolarization ratio spectra for cells in the three solutions are shown in FIG. 7B with relative intensities preserved. In the presence of BSA (FIG. 7B, BSA line), scattering from cells is significantly reduced in the red region of the spectrum. Addition of AA results in an overall increase in scattering (FIG. 7B, AA line).

The depolarization ratio spectrum of cells in BSA was fit to a linear combination of forward and backward Mie scattering components of nuclei plus a DC offset. The mean diameter of nuclei was determined by light microscopy (d=12.8±2 μm) and the refractive indices of the nuclei and the surrounding medium were varied to achieve the best fit. The best fit was obtained for relative refractive index of nucleus $n_{rel}$=1.036, and medium refractive index, which corresponds to the refractive index of the cytoplasm, $n_m$=1.374 (FIG. 7C, curve 390). The refractive index obtained from the fitting procedure ($n_m$=1.374) agrees well with the refractive index of BSA solution used in the experiment ($n_m$=1.37).

The refractive indices for nuclei and cytoplasm obtained in the experiments with cells in BSA were directly applied to fit the depolarization ratio spectrum of cells in PBS. The mean diameters of cells (d=19.0±2 μm) and of nuclei (d=12.8±2 μm) were determined using phase-contrast microscopy. The best fit was obtained varying only the coefficients for forward and backscattering components of both the nucleus and the cytoplasm and a DC offset value (FIG. 7D).

The depolarization ratio spectrum of cells in AA was fit to a linear combination of forward and backward Mie scattering components of nuclei and a DC offset using the mean diameter of nuclei d=11.0±2 μm. Note that the mean nuclear diameter is smaller than the nuclear diameter in PBS. The refractive index of the surrounding medium $n_m$=1.374 was used and the relative refractive index of nuclei was varied. The best fit was obtained for relative refractive index of nuclei $n_{rel}$=1.05 (FIG. 7E).

Figures 8A, 8B:
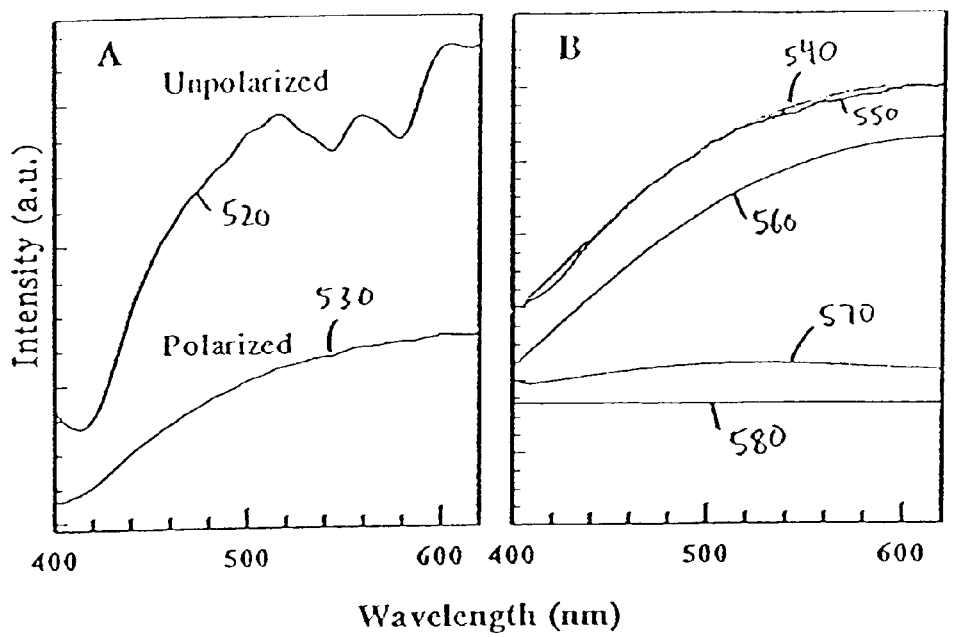
FIGS. 8A and 8B are plots showing measured reflectance spectra and Mie calculations for normal cervical biopsy: (A) reflectance spectra obtained using unpolarized (line 520) and polarized (line 530) illumination/detection; (B) depolarization ratio spectrum (line 550), calculated fit to equation (12) (line 540), forward Mie component of nucleus (line 560), forward Mie component of cytoplasm (line 570), and backward Mie component of cytoplasm (line 580). The theoretical curves are multiplied by coefficients extracted from the least-square algorithm used to achieve the best fits for the experimental data. Arbitrary DC offsets are added to theoretical curves in order to facilitate comparison within one plot.

FIGS. 8A–8B (see the Brief Description of the Drawings) illustrate the results obtained for a normal cervical biopsy. Strong hemoglobin absorption is evident in the reflectance spectrum obtained without the polarizer-analyzer in the collection channel (FIG. 8A, top curve). The spectrum is normalized to the reflectance from a diffuse scattering substrate to account for spectral characteristics of the excitation lamp and the spectrometer. Both the hemoglobin absorption and the diffuse background were significantly reduced after the parallel and the perpendicular components of the biopsy scattering were collected and the depolarization ratio was calculated (FIG. 8A, bottom curve). The resulting scattering profile could be described using Mie theory with the refractive indices derived from the experiments with cells (refractive index of the surrounding media $n_m$=1.33, refractive index of cytoplasm $n_{cyt}$=1.374, a nucleus-to-cytoplasm relative refractive index $n_{rel}$=1.036). It was assumed that both the nucleus and the cytoplasm independently contributed to the scattering of the epithelium. A Gaussian distribution of sizes with standard deviation of 2 μm was used and the mean diameters of cytoplasm and nuclei were varied in Mie theory calculations. The best fit was obtained for the diameter of nucleus $d_{nuc}$=8.0 μm and the diameter of cytoplasm $d_{cyt}$=19.0 μm (FIG. 8B). Note that arbitrary DC offsets are added to the theoretical curves presented in FIG. 8B in order to facilitate their comparison within one plot. It can be seen that the forward Mie component of nucleus closely resembles the experimental depolarization ratio spectrum. Mie theory calculations showed that the contribution of the forward Mie scattering from the nucleus is about 8 times higher relative to the forward component of the cytoplasm. Thus, it can be concluded that the scattering from the epithelium is mainly determined by the scattering from nuclei. The backscattering components of both the nucleus and the cytoplasm were found to be flat and featureless as compare to the forward components. It is important to note that in the inventors' model it was assumed that the depolarization ratio of the diffusely scattering background from stromal layer is wavelength independent. To confirm this assumption the inventors measured the depolarization ratio of stroma for a normal cervical biopsy and found that it was spectrally flat relative to the depolarization ratio of the epithelial layer.

Figures 9A, 9B:
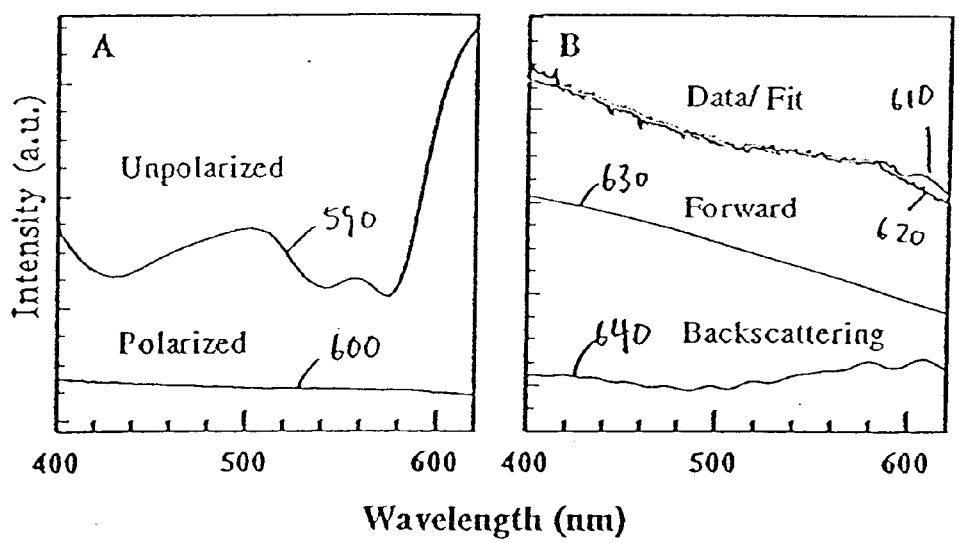
FIGS. 9A and 9B are plots showing oral cavity reflectance spectra obtained in vivo and corresponding Mie theory calculations: (A) reflectance spectra obtained using unpolarized (line 590) and polarized (line 600) illumination/detection. (B) Polarized reflectance spectrum (line 620), calculated fit to equation (12) (line 610), forward Mie component of scattering of nucleus (line 630), and backscattering Mie component of nucleus (line 640). Arbitrary DC offsets are added to the theoretical curves in order to facilitate comparison within one plot.

In vivo measurements of oral cavity mucosa are summarized in FIGS. 9A–9B (see the Brief Description of the Drawings). As in the case of in vitro tissue measurements, the use of polarized illumination/detection significantly reduces the contribution of hemoglobin absorption to the reflectance spectra (FIG. 9A, compare curves 590 and 600). Since biopsy data suggest that nuclei determine epithelial tissue scattering, only the nucleus was used to fit the scattering profiles obtained in vivo. The mean diameter of nuclei was an unknown parameter in Mie theory calculations and was found to be 5 μm. A Gaussian distribution of sizes with 1 μm standard deviation was used.

The nuclear diameters of 8 μm and 5 μm obtained from Mie theory calculations for the cervical biopsy and in vivo measurements, respectively, agree reasonably well with previously reported value of 6.1±0.7 μm obtained from morphometric measurements of normal squamous cervical epithelium.

Results presented in FIGS. 8 and 9 (see the Brief Description of the Drawings) demonstrate that polarized reflectance spectroscopy may be used to detect the scattering properties of the epithelial layer in the presence of both a strong diffusely scattering background and hemoglobin absorption. The resulting scattering spectra can be described by Mie theory using nuclear sizes of epithelial cells as unknown parameters. The best fits to experimental data provide information about the nuclear size distribution which is a key quantitative morphologic characteristic used by pathologists in detection of pre-cancerous lesions. The approach disclosed herein is based, at least in part, on the fact that few scattering events do not significantly alter the polarization of incident light while multiple scattering leads to depolarization. Only few scattering events can occur in the epithelial layer, whereas light that penetrates deeper in the tissue undergoes multiple scattering by stroma as well as absorption by hemoglobin. When polarized excitation is used, the portion of the reflectance spectrum with polarization parallel to the polarization of the illumination light consists of light scattered by epithelial cells and a diffuse background signal from stroma which is modulated by hemoglobin absorption. At the same time the component of the reflectance spectrum with polarization perpendicular to that of the incident light polarization contains only the diffuse background scattering. Thus, the scattering size-dependent characteristics of the epithelial layer can be obtained from the depolarization ratio.

This example demonstrates that depolarization ratio spectra can be used to extract size-dependant periodic Mie scattering of polystyrene beads in the presence of much stronger diffuse scattering from the substrate. Polystyrene spheres provide a good first model to study because their sizes and refractive indices are well known and their scattering spectra are well described by Mie theory. Comparison of scattering spectra of diluted suspensions of polystyrene beads with their highly packed semi-regular monolayers revealed a new periodic component which is not described by Mie theory for individual beads. The inventors believe that this periodicity is related to the spacing between beads in the monolayer and, thus, similar behavior could also be observed in other systems consisting of regular spaced scatterers.

Next, the inventors analyzed scattering of cell suspensions whose refractive indices are much smaller than polystyrene beads and whose internal structure is more complex. In general, the exact solution for elastic scattering of light by a cell is determined by the cell size and the three-dimensional distribution of refractive indices inside the cell. However, the inventors' results show that scattering from cells can be described using a simplified model where a cell is treated as two independent, spherical scatterers: a nucleus and a cytoplasm which are described using average refractive indices. It was shown that the forward scattering of cells can be adequately described using Mie theory calculations with average refractive indices of nucleus and cytoplasm. However, the situation is more complicated for backward scattering where the fluctuations of the refractive index inside cell and scattering from organelles smaller than nucleus become increasingly important.

In the inventors' model it was assumed that cells and nuclei are spherical objects and, thus, do not depolarize light after a single scattering event. In fact, cells are not strictly spherical. For example, it was reported that normal squamous epithelial cervical cells have ellipsoidal shape with major to minor axis ratio of about 1.3. In general, polarization of light can be altered as a result of backscattering at large angles from ellipsoidal particles with the maximum depolarization effect for ellipsoids with major to minor axis ratio of about 2. The depolarization decreases as the shape parameter approaches the value of 1 or infinity. However, it has been noted that the depolarization is very small for nonspherical particles with a refractive index close to 1. Recent polarization measurements of tissue phantoms and in vitro tissue also indicated that the nonspherical nature of the scatters in biological tissue does not cause major perturbation of polarization in scattering of light.

The scattering of cell nuclei can be directly characterized when the optical interface between the cytoplasm and solvent is eliminated using BSA. The best fit provides refractive indices for both the nucleus and the cytoplasm which is the surrounding medium of nuclei. The inventors used the refractive indices obtained from the experiment with cells in BSA solution to describe the scattering of cells in a pure PBS buffer where both the cytoplasm and the nucleus contribute to the reflectance spectrum. Mie theory calculations were in good agreement with the experimental data. This result suggests that cell suspensions in BSA solution could be effectively used to determine refractive indices of different types of cells including cells at different stages of cancer development.

Dramatic decreases in both the hemoglobin absorption and the diffuse scattering were observed when polarized illumination/detection was used to analyze reflectance spectra of epithelial tissue in vitro and in vivo. The inventors demonstrate that the resulting scattering spectra can be described using Mie theory calculations with the refractive indices derived from the experiments with cell suspensions in BSA and PBS solutions. Initially, it was assumed that both the nucleus and the cytoplasm contribute to the scattering of the epithelium. However, Mie theory calculations for a cervical biopsy showed that nuclei determine the scattering properties of the epithelial layer (FIG. 8B, compare curves 550, 540, and 560). This result is not unexpected because it is more adequate to treat an epithelial layer which consists of densely packed cells as a continuous medium with refractive index of the cytoplasm and embedded nuclei rather than a suspension of isolated cells. Thus, only nuclei were used to fit polarized reflectance spectra obtained in vivo (FIG. 9B). The best fits resulted in mean diameters of nuclei which are in good agreement with previously reported morphometric analysis of normal epithelial cells where the mean diameter of about 6.1±0.7 $\mu$m were reported. Differences in mean diameters obtained from different sets of measurements could be attributed to individual variations from person to person.

In summary, the results of this example suggest that the use of polarized illumination and detection allows selective detection of the size-dependent Mie scattering of epithelial nuclei in vivo (and in vitro). Subsequent analysis of the Mie scattering component can provide information about the nuclear size distribution and nuclear morphometry—key parameters in histopathologic analysis of epithelium which currently can only be assessed through invasive, painful biopsy.

EXAMPLE 2

The following non-limiting example is included to demonstrate specific embodiments of the invention, and more particularly, specific embodiments relating to instrumentation according to the present disclosure. It should be appreciated by those of skill in the art that the techniques disclosed in the example which follow represent techniques discovered by the inventors to function well in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the invention.

This non-limiting example relates to a spectroscopy system that was designed and constructed in accordance with the present disclosure to make polarized reflectance measurements with a probe having a diameter smaller than 3.5 mm. The probe was built with three optical fibers—one excitation and two collection fibers The excitation and one of the collection fibers was covered with a polarizing film with parallel polarization; the other collection fiber was covered with a polarizing film with perpendicular polarization.

Measurements were made in diluted solutions of 5 micron polystyrene beads, on skin and on oral cavity with a pulsed excitation light source. The presence of a pulsed light source eliminated almost entirely the influence of room light on the measurements. Results showed the correctness of the theory used; spectra compared well with the results of a non portable optics bench system. In vivo measurements carried out on three volunteers showed that this system would be portable in clinical environments.

Setup of the Tip of the Probe

Figures 10A, 10B:
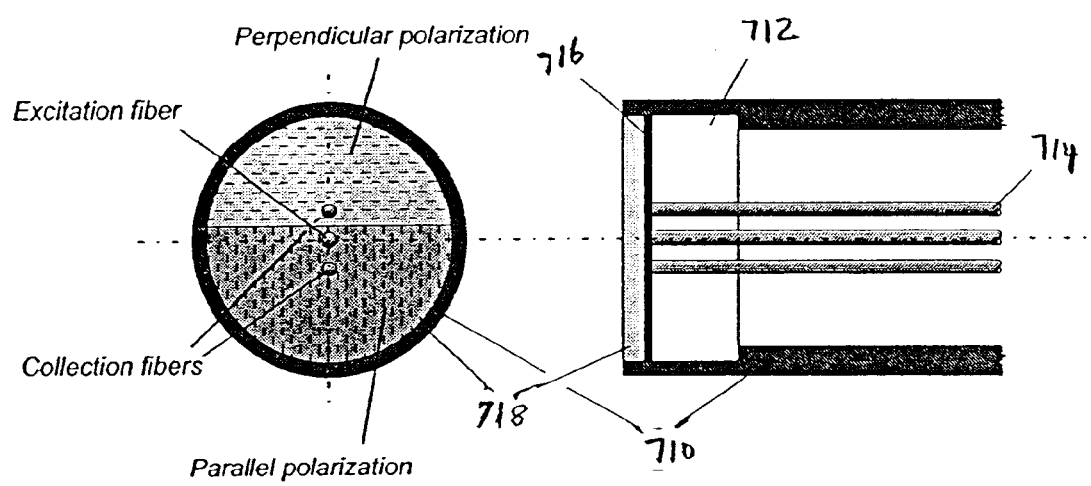
FIGS. 10A and 10B are shematics showing general configuration of the tip of a fiber optic probe according to one embodiment of the present disclosure. Three fibers are glued each in their hole of a fiber disc. Afterwards, two pieces of polarizing film are glued on the polished disc surface, one piece in a parallel and one in a perpendicular polarized direction. For the protection of the film, a fused silica cover glass disc is glued on the film.

Two requirements were desired in the construction of the probe of this example; namely, that it should be possible to make measurements with polarized light and that the probe has a minimal tip diameter. The minimal configuration is given by one excitation fiber and two collection fibers. The excitation fiber is used to deliver polarized light to tissue and the two collection fibers collect and guide the remaining reflected light to a spectrograph. Linear polarizers, oriented orthogonally with respect to each other, are located in front of the two collection fibers as shown in FIGS. 10A and 10B. Backscattered light is filtered through the linear polarizers before entering the fibers.

In this embodiment, the whole tip consists of 5 different parts, which are a tubing of stainless steel (710), a fiber disc (712) which holds the three fibers (714), the polarizing film (716) and a cover glass, or optical window, for the protection of the film (718). The polarizing film is divided into two parts. One part covers the excitation and one of the collection fibers (parallel polarization on FIGS. 10A and 10B). The other part just covers one of the collection fibers (perpendicular polarization on FIGS. 10A and 10B). In this configuration, it is possible to deliver linear polarized light and at the same time measure its parallel and perpendicular orientation of the reflected light.

Figure 11:
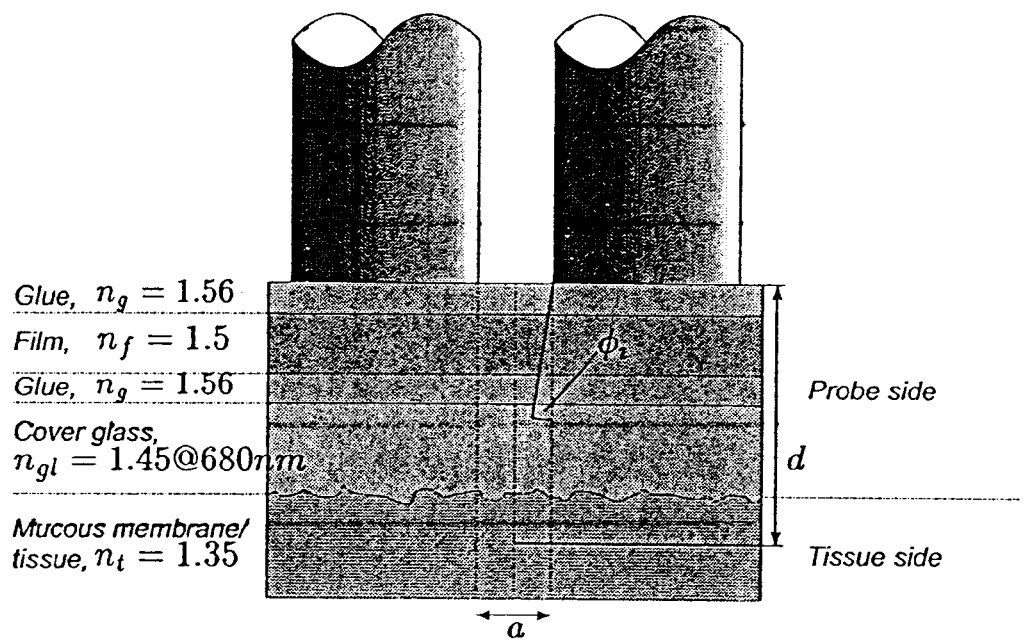
FIG. 11 is a schematic showing the transition between a fiber optic probe according to one embodiment of the present disclosure and tissue. The overlapping zone between the light cones of the fibers depends on the distance between the fibers and the materials light goes through (refractive index). The distance between the fibers depends on the aperture angle and the distance between a fiber end and the cone intersection.

The distances between the fibers are calculated on the basis of the different layers which are irradiated by the light (polarizing film, cover glass, tissue). An important requirement is that the outgoing light cone from each fiber does not overlap with the neighbor fiber cone in a tissue depth range of 1–50 microns (Fresnel reflection). A detailed view of the different layers and their refractive indices is shown in FIG. 11. The distance calculation between the fibers is based on Snell's law.

These calculations showed that the aperture angle only depends on the NA of the fiber and the refractive index of the mucous membrane (see FIG. 11), $$\phi_i = \arcsin\frac{NA}{n_t}$$

with NA=0.22 and $n_t$=1.35. This results in an aperture angle of $°\phi_1$=9.38 degrees. Together with the distance between the fiber ends and the cone intersection d, it is possible to calculate the distance a between the fibers. Table 2 shows three different assumptions for the thicknesses of the different layers. For the final layout of the three fibers a mean value between the worst- and the best case, ~100 μm, was chosen.

TABLE 2

| Layer | Worst Case (μm) | Best Case (μm) | Used Case (μm) |
|---|---|---|---|
| Glue | 10 | 1 | 10 |
| Film | 70 | 65 | 70 |
| Glue | 10 | 1 | 10 |
| Cover Glass | 185 | 160 | 185 |
| Tissue | 50 | 1 | 10 |
| Total | 325 | 228 | 285 |
| Distance between fibers | 107 | 75 | 94 |

The fiber disc consists of stainless steel and was made by laser cutting. First the three fibers are glued (a glue such as EPO-TEK 301-2, from Epoxy Technology, Inc., Billerica, Mass. may be used for this) each in its hole. Afterwards the disc was polished for an optimal fiber surface. The central part of the probe, the polarizing film, is also glued on the disc surface. The film is divided in two pieces, one in a parallel (covers the excitation fiber and one collection fiber) and another in a perpendicular (covers the second collection fiber) polarized direction. For the protection of the film, a fused silica cover glass ($n_{gl}$=1.45 @ 680 nm, available from Quartzplus, Inc., Brookline, N.H.) is glued on the polarizing film. The whole construction is held together by a stainless steel tubing.

Lamp and Optical Construction

The lamp which is used in this example is a 60 W Xenon flash lamp (available from Hamamatsu Corporation, Japan). The whole optical construction is screwed on the lamp housing.

The optical construction is based on basic calculations on plano-convex lenses known in the art. The specifications of the lenses used in this configuration are listed in Table 3.

TABLE 3

| Lens | Manufacturer | Focal length | Entrance Pupil |
|---|---|---|---|
| Collecting lens | CVI Laser Corp. | 25 mm | 25.4 mm |
| Focusing lens | Linos-Photonics Inc. | 40 mm | 21.4 mm |

Building a Polarized Reflectance Probe

It is quite difficult to build a probe in the dimensions of mm and μm, without using high precision instruments. Nevertheless it was possible to develop some simple techniques for building the probe of this example. Before describing every single construction step in detail, the next section gives a short overview about the parts of the probe which have been manufactured by different firms.

Manufacturing of the Fiber Disc, the Cover Glass and the Tubing

The probe primarily includes a stainless steel tubing, a fiber disc to fix the three fibers, and a cover glass to protect the polarizing film from direct contact with tissue.

The fiber disc with a diameter of 0.134 in (~3.40 mm) and a thickness of 0.06 in (~1.52 mm) is made of stainless steel and has three holes each with a diameter of 0.01 in (~254 μm). The holes of these small dimensions were made by laser drilling (LAI Companies, Westminster, Md.). The diameter of the holes is deliberately a little bit bigger than the fiber itself, having enough space for gluing the fibers into the holes.

The protecting cover glass with the same diameter as the fiber disc and a thickness of about 0.006 in (~160 μm) was manufactured by Quartzplus, Inc. (Brookline, N.H.) and is made of fused silica. The fiber disc as well as the cover glass are glued into a counter bored stainless steel tubing (Small Parts, Inc.). The diameter of the counter bored hole was made on a lathe having an inner diameter of 0.135 in (~3.42 mm). The depth of the counter bored hole was about 0.069 in (~1.75 mm).

Gluing and Polishing the Fibers into the Fiber Disc

The first step in constructing the polarized reflectance probe was gluing the three fibers (Fiberguide Industries, each about 4 m long) into the fiber disc with a F112 epoxy (Thorlabs Inc.). Before gluing, the fit between the fibers and the fiber disc had been tested. The fibers were slipped into the three holes of the disc. If the optical fiber did not fit into the disc the jacket from the fiber was stripped to reduce its diameter. After the fit testing had been successfully done, the F112 Epoxy was prepared. The separator bar on the epoxy BI-PAX was removed and the two parts were mixed by rubbing the package on the edge of a work table for about one minute. After the epoxy had been thoroughly mixed, the corner of the BI-PAX had been cut of in preparation for loading the syringe.

The fibers were now glued into the fiber disc. The disc should be cleaned by placing it in a glass beaker and covering the disc with ethyl alcohol. The fibers themselves also should be cleaned by moistening wipes with ethyl alcohol and carefully wiping the dust off.

After the glue had dried, the disc was polished by using a four step polishing process. First of all, the polishing glass plate was cleaned with a lint-free towel moistened with ethyl alcohol. The polishing films were cleaned in the same way. Afterwards the fibers were pulled through the polishing tube, and the tube was mounted itself to the polishing disc.

Now the polishing could be started. The first step began with a 5 $\mu$m lapping film. This step quickly removed excess epoxy from the tip of the disc. The first step ended when only a thin layer of epoxy remained on the surface of the disc. The next step used a 3 $\mu$m lapping film to polish the disc until the edges of the epoxy bead began to break up. The following step used a 1 $\mu$m lapping film with three or four drops of water. The disc was lightly polished on the 1 $\mu$m until all the epoxy was removed from the disc. A final optional step could be performed on dry 0.3 $\mu$m lapping film.

After every polishing, the polishing plate as well as the polishing disc should be cleaned with ethyl alcohol.

After polishing, the disc was removed from the polishing tube and its surface was looked at using an inspection microscope. The following should be ensured:

1. The disc end surface should be free of epoxy.
2. There should be no heavy scratches through the core of the fiber.

If the disc failed to pass the inspection, the polishing was repeated using the 1 $\mu$m and 0.3 $\mu$m lapping film.

Gluing the Polarizing Film on the Fiber Disc

Gluing the polarizing film on the fiber disc was the most difficult part of the construction because there was no sure method that gluing would succeed the first time. In particular, removing the fiber disc from the microscope slide was time consuming and had to be done with patience.

First of all, a microscope slide had to be prepared to tape the two parts of polarizing film (perpendicular and parallel) on it. A piece of double sided tape was used to hold the polarizing films in fixed positions. The direction of the polarizer could be found by folding it parallel to the molecules alignment on the film. This flexure of the film resulted in a straight line on it. Cutting the film perpendicular to the mentioned line, the two pieces of film with an exact right angle on one side had to be joined onto the tape.

One should be sure that the tightness of the tape is not too strong otherwise it is not possible to remove the disc without destroying the film. Before putting the two polarizing films on the tape, touch the tape surface several times.

After preparation of the slide with the polarizer taped on it, the slide was glued onto a mounting stage. Therefore it was possible to focus the film under a microscope (Olympus BX40). Having the transition between the parallel- and the perpendicular polarizer in focus, the polishing disc, which held the polishing tube as well as the fiber disc in it, could be aligned. Now it was possible to position the film transition between two of the three disc holes.

For gluing the film onto the fiber disc, a special optical two component glue was used (EPO-TEK 301-2, Epoxy Technology) that could be cured with or without heat. After inspecting the fiber disc relative to the transition between the polarizers, the disc could be glued on the film by putting a drop of optical glue on the disc. Afterwards the translation stage of the microscope was moved and pressed against the polarizing film that two holes cover the parallel and one hole the perpendicular polarizing film. This configuration had been kept in place for at least two days. After the glue had dried out the slide could be carefully removed from the mounting stage.

During gluing there should be no bubbles between the disc and the film. Bubbles could lead to misinformation because of different refractive indices between air and glue. Whether there would be bubbles or not between the disc and the film could be seen by inspecting the gluing process through the microscope. It was also necessary that before gluing, both the disc and the film surface had been cleaned to remove dust (Leeds, lens cleaner).

Gluing the Disc into the Probe Tubing

The fiber disc was very fragile such that removing the disc from the slide was tricky. There was no guarantee this step would succeed the first time. In the case of a miss, gluing and polishing had to be done again. The easiest way was taking a scalpel and cutting off the tape around the disc. Afterwards the disc could be removed very carefully from the slide. The main reason for a miss would be when the tightness of the tape was too strong so that the polarizer remained on the tape.

Before gluing the disc into the tubing, its counter bored tip was inspected and cleaned in ethyl alcohol. Afterwards the fiber ends were slightly pushed through the tubing and the fit of the disc was tested. To glue the disc into the counter bored hole the same epoxy could be used as described earlier. Some glue was put on the inner surface of the counter bored hole and the fiber disc was pressed into the hole. This configuration had been again kept in place for at least two days.

Preparing the Protecting Kevlar Tubing

The difficult part in this step was constructing a transition which enables the fibers to bifurcate because every fiber had been connected to its own SMA connector.

First the three fibers were inserted into a 3 mm Kevlar tubing (Thorlabs Inc.) with a length of about 2.5 m. One end of the Kevlar tubing was glued (3M, Super Glue Gel) into the stainless steel tubing and afterwards, a shrink tubing strengthened the transition.

The fibers which came out of the Kevlar tubing (~1.5 m) were each first protected by a yellow 900 $\mu$m furcation tubing (Thorlabs Inc.) and second by a Kevlar tubing again. The bifurcation was again strengthened by a shrink tubing. On top of that a hard core transition was constructed to further protect the bifurcation. This hard core transition was just the rear part of a pen and could be built very easily by cutting it into two pieces. Finally the pen was filled with a silicone rubber after the Kevlar tubings were stuck in the transition from both sides.

It was very important to pay attention to the bifurcation because there a fiber could break very easily.

Final Assembly

Now it was possible to push the connectors (Thorlabs Inc.) onto the fibers. Gluing the cover glass on top of the fiber was again a delicate matter. The most important step was that there was no glue in the center of the window where the fibers are. It was possible to use the same glue (EPO-TEK 301-2) which was used to glue the film on the disc.

Only a small quantity of glue should be put on the tip of the probe; otherwise, the glue would flow into the center of the window.

Because this probe would be used in future to take patient measurements it would be very important that after an examination the probe could be sterilized. Some experiments were made with a common sterilizer (Cidex) together with the polarizing film and the used glue (EPO-TEK). It was determined that the film was destroyed by this sterilizer. In order to avoid getting the film in touch with the sterilizer, the edge between tubing and cover glass was filled again with the EPO-TEK 301-2 which on the one hand resists the sterilizer, on the other hand is dermatological compliant.

Measurements Made with Probe

Measurements were first made with diluted solutions of 5 μm polystyrene beads; afterwards, measurements in vivo, on skin and on oral cavity were performed.

Configuration

Figure 12:
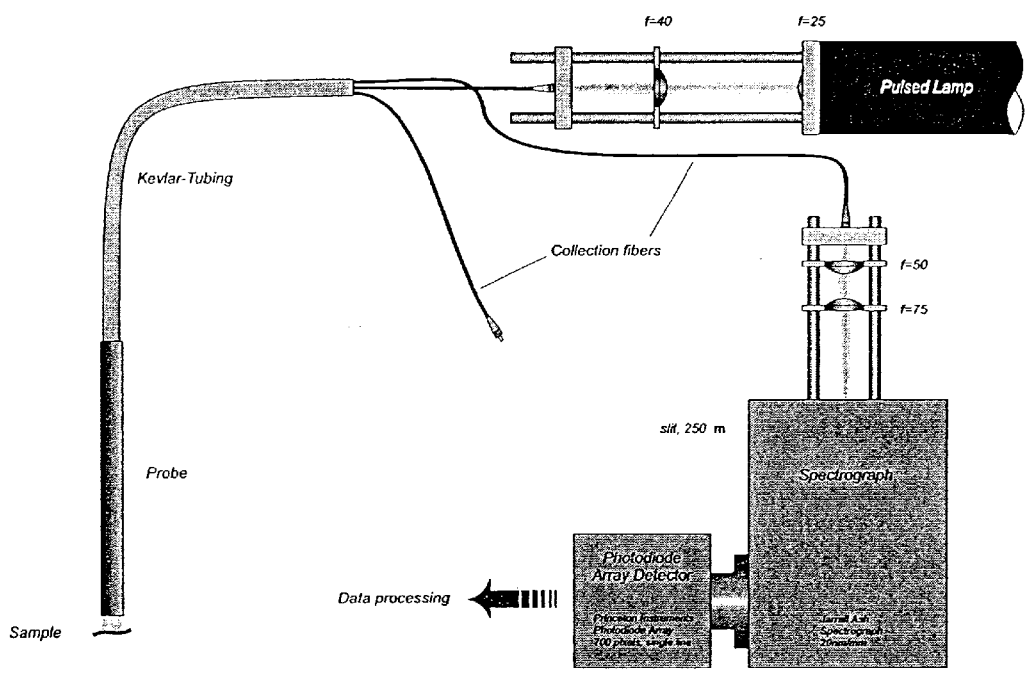
FIG. 12 is a diagram showing one configuration for probe measurements in accordance with the present disclosure.

Measurements were made with the configuration shown in FIG. 12. The excitation fiber of the probe was connected to the illumination lamp and one of the collection fiber was connected to the spectrograph. After the first measurement with either the parallel or the perpendicular fiber channels was made, the second collection fiber was connected to the spectrograph, and the whole measurement was repeated again.

While studying the data, it determined that it is important whether or not there is a gap or not between the probe tip and the surface of the measured object. It has also to be mentioned that some of the following experiments were also made using a cw-lamp as the illumination light source. The reason for this change was the instability of the pulsed light source after running it for some hours.

Water and Solution of Beads

The steps taken to make the measurements for water and solutions of beads were generally as follows:
1. Measure parallel channel
2. Measure perpendicular channel
3. Measure background
4. Calculate depolarization ratio D [(I(parallel)−I(perpendicular))/(I(parallel)+I(perpendicular))]

Measurements with water and solutions of beads were made both in cw- and pulsed light. The settings in Table 4 were used.

TABLE 4

|  | cw-light | pulsed light |
|---|---|---|
| Room light status | off | on |
| # accumulations | 1000 | 500/1000/2000 |
| Exposure time | 60 ms | 30 ms |
| Frequency | — | 30 Hz |
| Gate delay | — | 7500 ns |
| Gate width | — | 3750 ns |
| Gap | with/without | with/without |

In vivo Measurements

For in vivo measurements it is important to see how common absorption of both channels such as blood could be eliminated by subtracting the normalized perpendicular measurements from the normalized parallel measurements. The normalization of the collected data was based on dividing both, the parallel- and the perpendicular measurements by the sum of the parallel- and the perpendicular measurements made on the LRS substrate according to the following formula:

$$d_{\|}(\lambda) = \frac{I_{\|}(\lambda)}{I_{w\|}(\lambda) + I_{w\perp}(\lambda)}$$

$$d_{\perp}(\lambda) = \frac{I_{\perp}(\lambda)}{I_{w\|}(\lambda) + I_{w\perp}(\lambda)}$$

By subtracting the normalized perpendicular intensity from the normalized parallel intensity, $$n(\lambda) = d_{\|}(\lambda) - d_{\perp}(\lambda),$$

it was possible to express something about the "quality" of the blood absorption.

The in vivo measurement sequence looked like this:
1. Measure parallel channel
2. Measure perpendicular channel
3. Measure water background, parallel
4. Measure water background, perpendicular
5. Calculate d(λ)

In vivo measurements settings are shown in Table 4.

Summary

This example describes step-by-step construction descriptions for a polarized reflectance probe. It is possible to build this probe without having high precision instruments. The constructed probe has been tested on the basis of reference measurements which have been done on an existing test system in both cw- and pulsed light modes. Running the setup in pulsed mode, a pulsed light source with a stable light output has been used.

EXAMPLE 3

The following non-limiting example is included to demonstrate a specific embodiment of the invention. It should be appreciated by those of skill in the art that the techniques disclosed in the example that follow represent techniques discovered by the inventors to function well in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the invention.

This example is aimed at using polarized reflectance spectroscopy to selectively detect the size-dependant scattering signatures of epithelial cells in-vivo to obtain diagnostically useful morphologic information. Because of its easy accessibility, pre-cancer detection of the oral cavity is considered; however, one having ordinary skill in the art will recognize that the techniques described herein apply to other samples as well, including other biological tissues.

This example involves at least the following steps: (a) measuring polarized reflectance spectra to characterize the size-dependant scattering of normal and neoplastic cells and oral cavity biopsies, (b) developing methods based on Mie theory to extract quantitative morphologic information from polarized reflectance spectra of epithelial tissue, and (c) designing and constructing a fiber optic probe for polarized reflectance measurements. The probe will be used to validate the approach in clinical studies of oral cavity. Areas examined will be biopsied and analyzed using quantitative pathology as the "gold standard."

This example, in conjunction with the rest of this disclosure, may provide clinicians a tool for non-invasive, real time in-vivo histologic analysis via reflectance spectroscopy that can be extended to many other organ sites.

This example may build upon techniques that use specific molecular contrast agents to enhance optical imaging of pre-cancers. These agents may be based on specific molecular recognition between cancer specific molecular targets on the surface of epithelial cancer cells and labeled probe biomolecules. The combination of imaging optical techniques with the cancer specific contrast agents may increase the optical contrast between the normal and neoplastic tissue and may provide useful molecular-specific information to assist clinicians in earlier detection of pre-cancers. Thus, techniques of this disclosure may significantly improve specificity and selectivity of epithelial pre-cancer detection as compared to traditional techniques. To achieve this goal, at least the following specific may be carried out: (a) molecular specific contrast agents for pre-cancer detection may be validated using three-dimensional tissue phantoms, (b) an optical digital imaging device may be built to perform measurements on human epithelial tissue stained with the cancer specific agents, (c) the principles of measurements of human tissue with polarized illumination/detection may be used in the design and/or development of the imaging instrument, and (d) the combination of the optical digital imaging instrumentation and the proposed contrast agents may be tested on human biopsies and excised specimens from human body as a result of a surgical procedure.

In summary, the optical spectroscopic and imaging techniques of the present invention and of this example may significantly benefit the health care by reducing the number of unnecessary biopsies, enabling combined diagnosis and therapy, and reducing the need for clinical expertise. All these advantages may ultimately benefit patients by providing more effective health care and reducing the health care costs.

As made apparent by publication in the art, it is highly desirable to develop experimental techniques that allow elastic light scattering of epithelial cells to be measured directly. The techniques described herein may be used to develop such experimental tools. These techniques may provide a tool to selectively measure the singly scattered light associated with the epithelium. Reflectance from the skin surface and the light diffusely scattered by the underlying dermis can be separated when polarized illumination and detection are used. When skin is illuminated with linearly polarized light and viewed through a linear polarizer aligned parallel to the polarization of the incident light, surface texture and details are enhanced. When viewed through a linear polarizer aligned perpendicular to the polarization of the incident light, blood vessels and pigmented lesions beneath the skin surface can be seen. In this example and disclosure, the use of polarization sensitive light scattering spectroscopy may be explored to directly measure the size-dependent elastic light scattering from the upper epithelial layer in vivo. This approach may reduce the contributions of multiple scattering and hemoglobin absorption produced by the stroma.

This example involves the measurement of the wavelength dependence of scattering with polarization parallel and perpendicular to the polarization of the illumination light. To extract the size-dependent characteristics of scatterers, the perpendicular component of scattered light may be subtracted from the parallel one. Mie theory calculations may be used to describe the observed scattering spectra and to estimate the sizes of the scatterers.

This example may involve at least the following parallel efforts: (1) mathematical modeling and (2) development of clinical instruments, culminating in one or more clinical trials.

Mathematical Modeling

The exact solution for elastic scattering of light by a cell is determined by the cell size and the three-dimensional distribution of refractive indices inside the cell. However, the inventors have found that scattering from cells may be adequately described using a simplified model where a cell is treated as two independent, spherical scatterers: a nucleus and a cytoplasm that are described using averaged refractive indices. The exact solution to the scattering is known in this case, and can be computed from Mie theory. This approach is used throughout this example.

In the model for this example, it is assumed that cells and nuclei are spherical objects and, thus, do not depolarize light after a single scattering event. In fact, cells are not strictly spherical. For example, it has been reported that normal squamous epithelial cervical cells have ellipsoidal shape with major to minor axis ratio of about 1.3. In general, polarization of light can be altered as a result of backscattering at large angles from ellipsoidal particles with the maximum depolarization effect for ellipsoids with major to minor axis ratio of about 2. The depolarization decreases as the shape parameter approaches the value of 1 or infinity. However, it has been noted that the depolarization is very small for nonspherical particles with a refractive index close to 1. Recent polarization measurements of tissue phantoms and in vitro tissue also indicated that the nonspherical nature of the scatters in biological tissue does not cause major perturbation of polarization in scattering of light.

Experimental spectra may be fit to a linear combination of forward and backward scattering components and a DC offset. Mie theory calculations may be used to compute the forward and backward theoretical scattering spectra. To account for the optical system's finite spectral resolution, computed curves (scattered intensity vs. wavelength) may be convolved with a Gaussian of width equivalent to the system's resolution (which, in one embodiment is FWHM=5 nm). In one embodiment, Mie theory calculations may be implemented using MATLAB. For each wavelength, calculations may be performed for a Gaussian distribution of scatterer sizes. Experimental data may then be fit to Mie theory calculations using a standard optimization algorithm.

Tissue Phantoms and Biopsies Studies

Polarized reflectance spectra may be measured from tissue models of oral epithelium at different stages of cancer development: normal, pre-cancerous, and malignant stages. Experiments may begin with cell suspensions placed atop a diffusely scattering substrate and may gradually progress to three-dimensional tissue models and biopsies from oral cavity. Normal and abnormal biopsies from oral cavity may be analyzed.

Suspensions of cancerous cells, pre-cancerous cells immortalized in various ways and normal cells from primary cultures may be measured in a pure PBS buffer and in the presence of BSA or acetic acid (AA). BSA may reduce the index mismatch between cytoplasm and extra-cellular fluid; this allows the scattering of nuclei to be directly accessed. AA is a contrast agent in clinical evaluation of pre-cancer and may be studied as a source of nuclear signal enhancement in polarized reflectance measurements. The components of scattered light polarized parallel and perpendicular to the incident light polarization may be collected, and the depolarization ratio may be used to analyze the data.

The depolarization ratio (D) is defined as:

$$D(\lambda) = \frac{I_{||} - I_\perp}{I_{||} + I_\perp} \quad (1)$$

where $I_{||}$ is the component of the scattered light polarized parallel to the incident light and $I_\perp$ is polarized perpendicular to the incident light. Size distributions for nuclei and cytoplasm may be determined using phase contrast microscopy. Mie theory calculations may be performed to fit the experimental curves for a range of realistic refractive indices of nucleus and cytoplasm. The refractive indices corresponding to the best fits may then be used to describe scattering of epithelial tissue in vitro.

It is important to note that the depolarization ratio can not be directly used to assess the scattering characteristics of the epithelial layer in the oral biopsies and in the in vivo measurements because both the parallel and the perpendicular components of the reflectance spectrum have strong contributions from hemoglobin absorption that dominate the depolarization ratio spectrum. Instead, the perpendicular component of light scattered by oral epithelium will first be subtracted from the parallel component and the result will be normalized to the total intensity of light (the perpendicular plus the parallel components) collected from a standard diffuse scattering substrate alone. The normalization will account for spectral characteristics of the excitation lamp and the spectrometer.

Clinical System Development

Figure 13A:
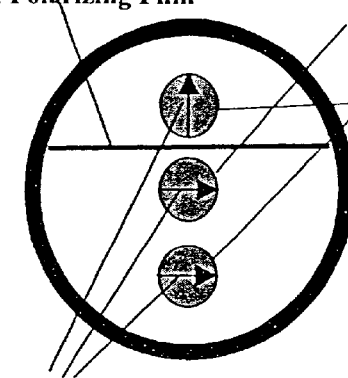
FIGS. 13A and 13B are diagrams showing general configurations of a tip of a fiber optic probe according to one embodiment of the present disclosure. The three fibers are glued each in their hole of the fiber disc. Afterwards two pieces of polarizing films are glued on the polished disc surface, one piece in a parallel and one in a perpendicular polarized direction. For the protection of the film, a fused silica cover glass disc is glued on the film.
Figure 13B:
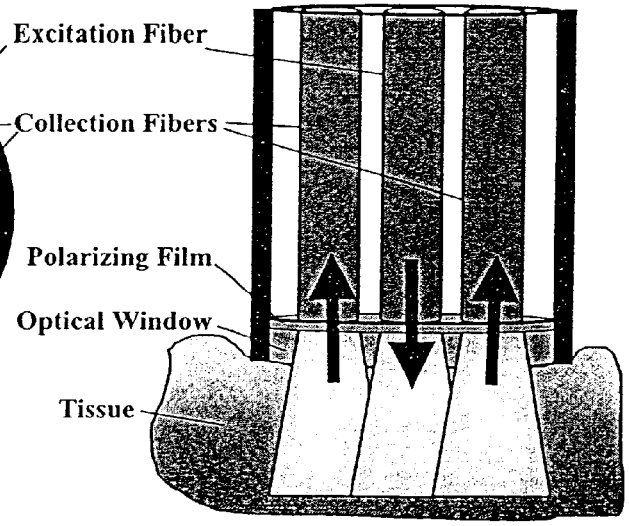

An optical probe design in accordance with the present disclosure is illustrated in FIGS. 13A and 13B. As shown, the probe includes a fiber delivering polarized illumination to the tissue site of interest and two independent fibers for simultaneous collection of parallel and perpendicular components of tissue scattering. The collection fibers may be located symmetrically relative to the excitation fiber. Two pieces of polarization film with polarization axes perpendicular to each other may be used to provide polarized illumination and polarization-sensitive detection. A quartz optical window may be placed on the top of the fiber probe.

There are two major considerations that should be taken into account in design and building of the probe. First, the distance between the illumination and collection fibers should be small to minimize collection of multiple scattered light and to maximize collection of light singly scattered in the epithelial layer. Second, the fiber NA and separation must be adjusted appropriately to avoid collection of Fresnel reflections from the window surface and the tissue front surface. The distance between the optical fibers, their numerical apertures, and the thickness of the optical window can be controlled. These parameters allow one to optimize the design of the optical probe to satisfy both requirements.

Other components of the spectrometer may include a pulse light source (Xenon lamp) to perform measurements under room light illumination, a spectrograph, a detector, and a computer. Such elements are shown, for example, in FIGS. 2 and 3. The device may be fabricated using an existing single grating monochromator (commercially available as Monospec 18, Jarrel Ash) and gated intensified photodiode array detector (commercially available as IRY-700, Princeton Instruments).

Clinical Trials

The optical probe of FIGS. 13A and 13B may be used to examine a group of normal volunteers. Next, pilot clinical studies may be performed, presenting pre-cancerous or cancerous lesions. Standard white light examination of the oral mucosa may be performed, noting any areas which are believed to contain dysplasia or cancer. Then, polarized reflectance measurements on 1–2 suspicious areas and at least one normal site may be performed. Suspicious sites may be biopsied and submitted for histopathologic diagnosis.

Based on the results of such a study, the sample size needed for a clinical trial with a statistically significant sample size to test the null and the alternative hypothesis may be evaluated. The null hypothesis is that polarized reflectance spectroscopy has the same sensitivity as currently used examination techniques. The alternative hypothesis is that spectroscopy is better. An anticipated sample size may be estimated using published studies on evaluation of fluorescence spectroscopy for pre-cancer detection in cervix. Based on these studies, it would require 81 patients to compare specificity of fluorescence spectroscopy and colposcopy using an alpha error of 0.05 and a power of 0.80. At this point, it is anticipated that a sample size of about 100 patients may be sufficient.

EXAMPLE 4

The following non-limiting example is included to demonstrate a specific embodiment of the invention. It should be appreciated by those of skill in the art that the techniques disclosed in the example that follow represent techniques discovered by the inventors to function well in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the invention.

Figure 14:
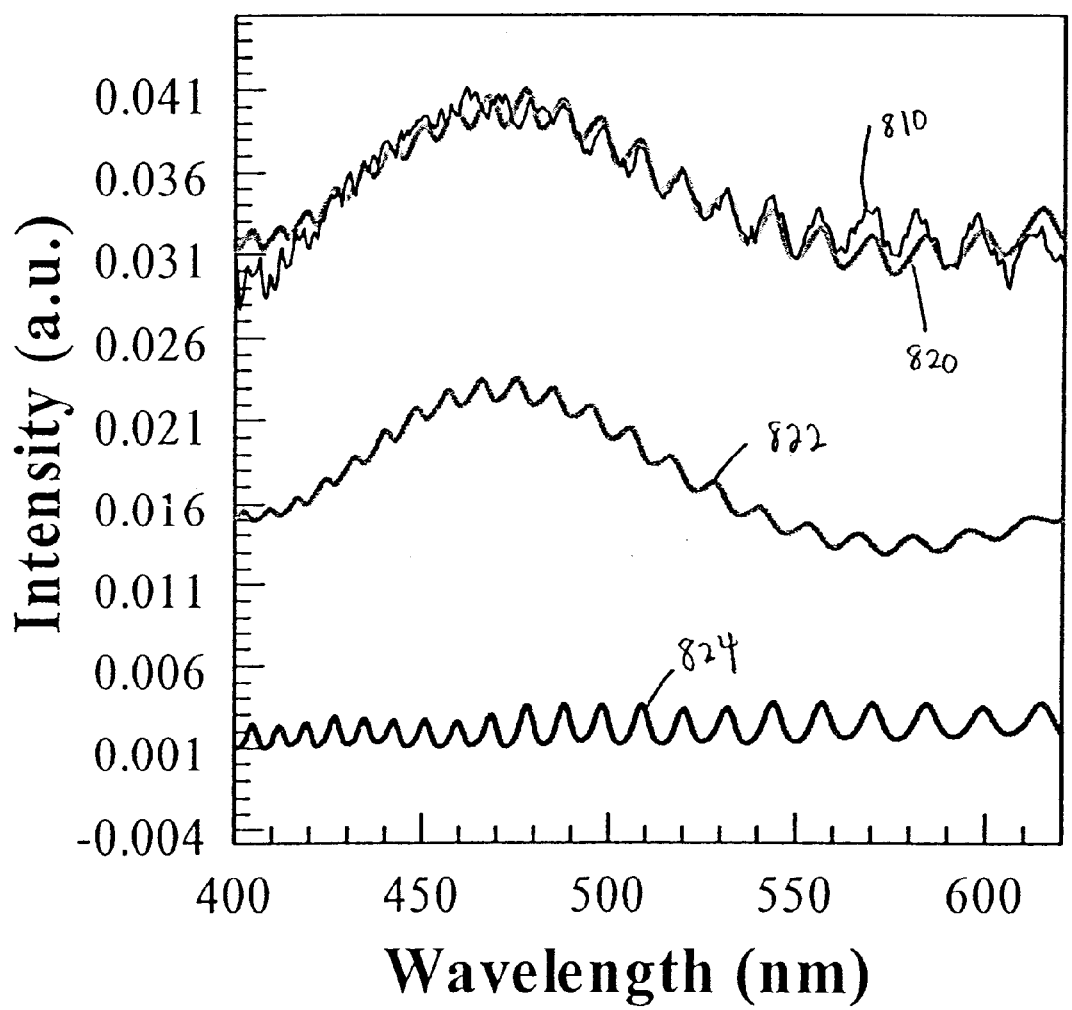
FIG. 14 is a graph showing an example of polarized reflectance measurements with a fiber optical probe according to one embodiment of the present disclosure. Five micron beads in water: experimental depolarization ratio (810); Mie theory fitting curve (820) and theoretical forward (822) and backscattering components (824) of the fit.

FIG. 14 is a graph showing an example of polarized reflectance measurements with a fiber optical probe according to one embodiment of the present disclosure. Five micron beads in water were studied. The graph of FIG. 14 shows the following: experimental depolarization ratio (810); Mie theory fitting curve (820) and theoretical forward (822) and backscattering components (824) of the fit.

Figure 15:
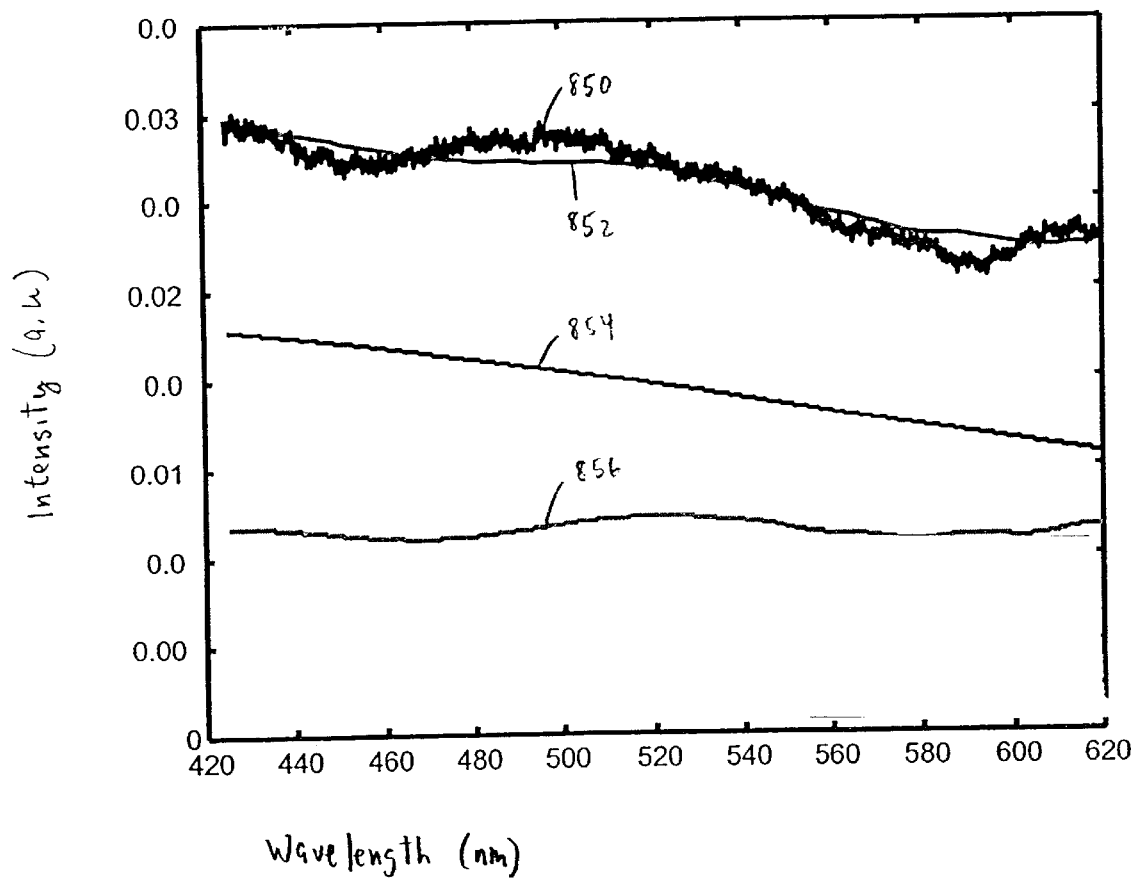
FIG. 15 is a graph showing an example of polarized reflectance measurements with a fiber optical probe according to one embodiment of the present disclosure. Oral cavity in vivo: experimental depolarization ratio (850); Mie theory fitting curve (852) and theoretical forward (854) and backscattering (856) components of the fit. The best fit was achieved for nuclear diameters d=5±0.2 $\mu$m.

FIG. 15 is a graph showing an example of polarized reflectance measurements with a fiber optical probe according to one embodiment of the present disclosure. Oral cavity in vivo was studied. The graph of FIG. 15 shows the following: experimental depolarization ratio (850); Mie theory fitting curve (852) and theoretical forward (854) and backscattering (856) components of the fit. The best fit was achieved for nuclear diameters d=5±0.2 μm.

Figure 16:
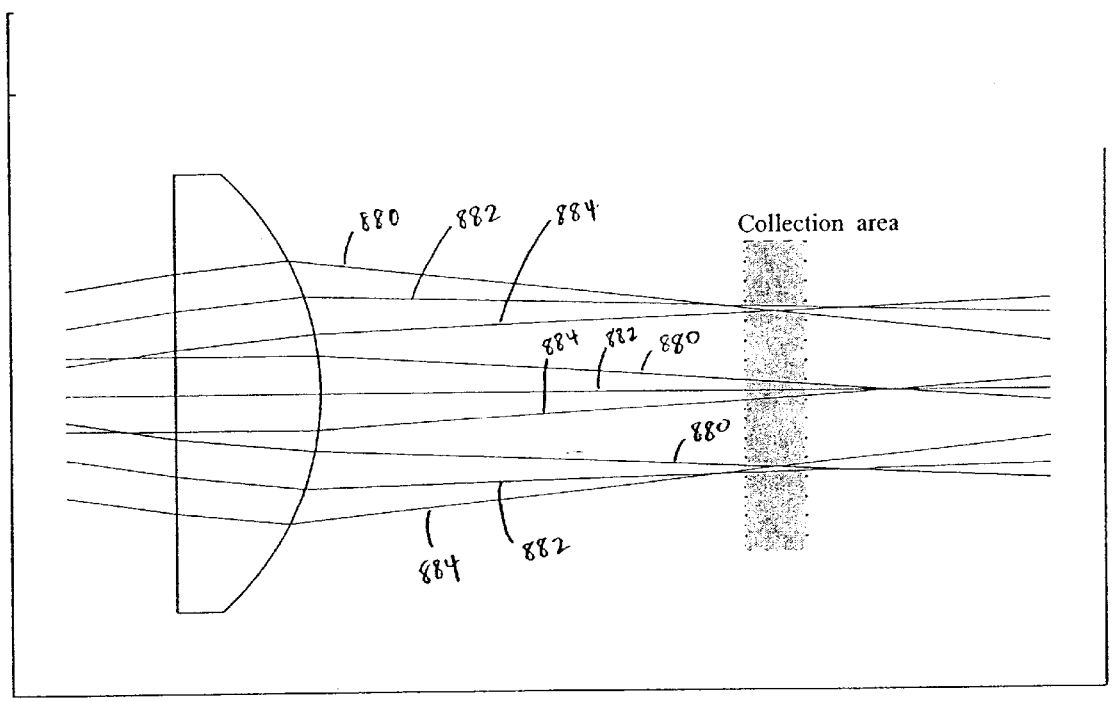
FIG. 16 is a diagram showing an example of an alternative fiber probe design with a lens according to one embodiment of the present disclosure. The lens is positioned in front of excitation and collection optical fibers to create an optimum overlap between an area illuminated by the excitation fiber and areas from which scattering is gathered by the collection fibers. Rays 882 show the path of excitation light and rays 880 and 884 show paths of scattered light which is detected by the collection fibers. The lens in this figure has a focal length of about 7.74 mm and a NA of about 0.0209.

FIG. 16 is a diagram showing an example of an alternative fiber probe design with a lens according to one embodiment of the present disclosure. The lens may be positioned in front of excitation and collection optical fibers to create an optimum overlap between an area illuminated by the excitation fiber and areas from which scattering is gathered by the collection fibers. Rays 882 show the path of excitation light and rays 880 and 884 show paths of scattered light which is detected by the collection fibers. The lens in this figure has a focal length of about 7.74 mm and a NA of about 0.0209.

All of the methods, systems, and apparatus disclosed and claimed herein can be made and executed without undue experimentation in light of the present disclosure. While the techniques of this invention have been described in terms of specific embodiments (and a specific example), it will be apparent to those of skill in the art that many variations may be applied to the disclosed methodologies and in the steps of the methods described herein without in any way departing from the concept, spirit and scope of the invention. For instance, methodology described herein may be applied not only to biological samples, but it may be applied to any samples in which scattering characteristics are to be analyzed. Biological samples may include both in vivo and in vitro samples. Various tissues may be analyzed including, but not limited to, the cervix and oral mucosa. Components of the apparatus disclosed herein may also vary, as is known in the art. The methodology disclosed herein may be adapted to computer software, as is known in the art, by utilizing, for instance coding to represent, for example, the equations of this disclosure. Likewise, methodology disclosed herein may be utilized as part of a system, including the apparatus of certain embodiments, a memory device used to store spectra information, and a microprocessor in communication with such a memory (the memory communicating with the microprocessor as is known in the art) to carry forth the calculations and analysis described herein.

References

The following references, to the extent that they provide exemplary procedural or other details supplementary to those set forth herein, are specifically incorporated herein by reference.

1. American Cancer Society (1993) Cancer Facts and Figures. Publication No. 93-400M, No. 5008-03.
2. J. R. Mourant, T. Fuselier, J. Boyer, T. M. Johnson, and I. J. Bigio, "Predictions and Measurements of Scattering and Absorption Over Broad Wavelength Ranges in Tissue Phantoms," Appl. Opt. 36, 949-57 (1997).
3. L. T. Perelman, V. Backman, M. Wallace, G. Zonios, R. Manoharan, A. Nusrat, S. Shields, M. Seiler, C. Lima, T. Hamano, I. Itzkan, J. Van Dam, J. M. Crawford, and M. S. Feld, "Observation of Periodic Fine Structure in Reflectance from Biological Tissue: A New Technique for Measuring Nuclear Size Distribution," Phys. Rev. Lett. 80, 627-630 (1998).
4. R. R. Anderson, "Polarized Light Examination and Photography of the Skin," Arch. Dermatol. 127, 1000-5 (1991).
5. http://omlc.ogi.edu/news/feb98/polarization/index.html
6. V. Backman, R. Gurjar, K. Badizadegan, I. Itzkan, R. Dasari, L. T. Perelman, and M. S. Feld, "Polarized Light Scattering Spectroscopy for Quantitative Measurements of Epithelial Cellular Structures In Situ," IEEE, J. Selected Topics in Quantum Electronics on Lasers in Medicine and Biology 5, (1999).
7. T. M. Johnson and J. R. Mourant, "Polarized Wavelength-Dependant Measurements of Turbid Media," Opt. Express 4, 200-216 (1999).
8. V. Sankaran, K. Schonenberger, J. T. Walsh, Jr., and D. J. Maitland, "Polarization Discrimination of Coherently Propagating Light in Turbid Media," Appl. Opt. 38,4252-4261 (1999).
9. G. Jarry, E. Steimer, V. Damaschini, M. Epifanie, M. Jurczak, and R. Kaiser, "Coherence and Polarization of Light Propagating Through scattering Media and Biological Tissues," Appl. Opt. 37, 7357-7367 (1998).
10. D. Bicout, C. Brosseau, A. S. Martinez, J. M. Schmitt, "Depolarization of Multiply Scattered Waves by Spherical Diffusers: Influence of the Size Parameter," Phys. Rev. E 49, 1767-1770 (1994).
11. R. Barer, "Refractometry and Interferometry of Living Cells," J. Opt. Soc. Am. 47, 545-56 (1957).
12. C. Smithpeter, A. Dunn, R. Drezek, T. Collier, and R. Richards-Kortum, "Near Real Time Confocal Microscopy of Cultured Amelanotic Cells: Sources of Signal, Contrast Agents and Limits of Contrast," J. Biomed. Opt. 3, 429-36 (1998).
13. H. D. Young. Statistical Treatment of Experimental Data. (McGraw-Hill, New York, N.Y. 1962).
14. H. van de Hulst. Light Scattering by Small Particles. (Dover, New York, N.Y. 1957).
15. R. Kudo, S. Sagae, O. Hayakawa, E. Ito, E. Horimoto, and M. Hashimoto, "Morphology of Adenocarcinoma in Situ and Microinvasive Adenocarcinoma of the Uterine Cervix. A Cytologic and Ultrastructural Study," Acta Cytol. 35, 109-16 (1991).
16. N. Wheeler, S. C. Suffin, T. L. Hall, and D. L. Rosenthal "Predictions of Cervical Neoplasia Diagnosis Groups. Discriminant Analysis on Digitized Cell Images," Analyt. Quant. Cytol. Histol. 9, 169-81 (1987).
17. E. Artacho-Perula, R. Roldan-Villalobos, J. Salas-Molina, and R. Vaamonde-Lemos, "Histomorphometry of Normal and Abnormal Cervical Samples," Analyt. Quant. Cytol. Histol. 15, 290-97 (1993).
18. L. Burke, D. A. Antonioli, B. S. Ducatman, Colposcopy. Text and Atlas, (Appleton & Lance, Calif. 1991).
19. A. Dunn, C. Smithpeter, A. J. Welch, R. Richards-Kortum, "FDTD Simulation of Light Scattering from Single Cells," J. Biomed. Optic. 2, 262-66 (1997).
20. R. Drezek, A. Dunn, and R. Richards-Kortum, "Light Scattering from Cells: Finite-Difference Time-Domain Simulations and Goniometric Measurements," Appl. Opt. 38, 3651-3661 (1999).
21. J. R. Mourant, J. P. Freyer, A. H. Hielscher, A. A. Eick, D. Shen, and T. M. Johnson, "Mechanism of Light Scattering from Biological Cells Relevant to Noninvasive Optical-Tissue Diagnostics," Appl. Opt. 37, 3586-3593 (1998).
22. A. Brunsting and P. F. Mullaney, "Differential Light Scattering from Spherical Mammalian Cells," Biophys. J. 14, 439-453 (1974).
23. J. M. Schmitt and G. Kumar, "Optical Scattering Properties of Soft Tissue: a Discrete Particle Model," Appl. Opt. 37, 2788-2797 (1998).
24. S. Asano and M. Sato, "Light Scattering by Randomly Oriented Spheroidal Particles," Appl. Opt. 19, 962-974 (1980).
25. S. L. Jacques, J. R. Roman, and K. Lee, "Imaging Superficial Tissues with Polarized Light," Lasers Surg. Med. 26, 119-129 (2000).
26. Sokolov K, Drezek R, Gossage K, Richards-Kortum R, "Reflectance Spectroscopy with Polarized Light: Is it Sensitive to Cellular and Nuclear Morphology," Optics Express 5, 302-317 (1999).
27. WHO Collaborating Centre for Oral Pre-cancerous Lesions (1978) Definition of leukoplakia and related lesions: an aid to studies on oral pre-cancer. *Oral Surg Oral Med Oral Pathol* 46, 518-39.
28. S. Silverman, M. Gorsky, and F. Lozada, "Oral leukoplakia and malignant transformation. A follow up study of 257 patients," Cancer 53, 563-68 (1984).
29. S. Lam, T. Kennedy, M. Unger, Y. E. Miller, D. Gelmont, V. Rush, B. Gipe, D. Howard, J. C. LeRiche, A. Coldman, and A. F. Gazdar, "Localization of Bronchial Intraepithelial Neoplastic Lesions by Fluorescence Bronchoscopy, "Chest 113 (2), 696-702 (1998).
30. S. Lam, C. MacAulay, J. Hung, J. LeRiche, A. E. Profio, and B. Palcic, "Detection of Dysplasia and Carcinoma In Situ with a Lung Imaging Fluorescence Endoscope Device," J of Thoracic & Cardiovascular Surgery 105 (6), 1035-40 (1993).

31. B. W. Pogue, G. C. Burke, J. Weaver, D. M. Harper, "Development of a Spectrally Resolved Colposcope for early detection of Cervical Cancer," in Biomedical Optical Spectroscopy and Diagnostics Technical Digest (Optical Society of America, Washington D.C. 1998), 87–89.
32. E. Dabelsteen, H. Clausen, and U. Mandel, "Carbohydrate Changes in Squamous Cell Carcinomas," APMIS Suppl. 27, 130–8 (1992).
33. J. L. Schwartz, "Biomarkers and Molecular Epidemiology and Chemoprevention of Oral Carcinogenesis," Crit. Rev. Oral Biol. Med. 11(1), 92–122 (2000).
34. T. Meyer and G. J. Rustin, "Role of Tumour Markers in Monitoring Epithelial Ovarian Cancer," Br. J. Cancer 82 (9), 1535–8 (2000).
35. K. J. W. Taylor and P. E. Schwartz, "Screening for Earlier Ovarian Cancer," Radiology 192, 1–10 (1994).
36. M. P. Boente, A. K. Godwin, and W. M. Hogan, "Screening, Imaging, and Early Diagnosis of Ovarian Cancer," Clinical Obstetrics and Gynecology 37 (2), 377–391 (1994).
37. M. C. Hung and Y. K. Lau, "Basic Science of HER-2/ neu: a Review," Semin. Oncol. 26, 51–59 (1999).
38. A. Berchuck, G. C. Rodriguez, A. Kamel, R. K. Dodge, J. T. Soper, D. L. Clarke-Pearson, and R. C. Bast, Jr., "Epidermal Growth Factor Receptor Expression in Normal Ovarian Epithelium and Ovarian Cancer. I. Correlation of Receptor Expression with Prognostic factors in Patients with Ovarian Cancer," Am. J. Obstet. Gynecol. 164, 669–674 (1991).
39. Y. Jin, F. H. White, and L. Yahg, "A Histological Morphometric Study of Nuclear Size in Benign and Malignant Neoplasms of the Human Cheek," Histopathology 23, 271–274 (1993).
40. M. R. Parkhurst and W. M. Saltzman, "Quantification of Human Neutrophil Motility in Three-Dimensional Collagen Gels: Effect of Collagen Concentration," Biophys. J. 61, 306–315 (1992).
41. R. Langer and J. P. Vacanti, "Tissue Engineering," Science 260, 920–926 (1993).
42. R. M. Kuntz and W. M. Saltzman, "Neutrophil Motility in Extracellular Matrix Gels: Mesh Size and Adhesion Affect Speed of Migration," Biophys. J. 72, 1472–1480 (1997).
43. J. Riesle, A. P. Hollander, R. Langer, L. E. Freed, and G. Vunjak-Novakovic, "Collagen in Tissue-Engineered Cartilage: Types, Structure, and Crosslinks," J. Cell. Biochem. 71, 313–327 (1998).
44. I. J. Bigio and J. R. Mourant, "Ultraviolet and Visible Spectroscopies for Tissue Diagnostics: Fluorescence Spectroscopy and Elastic-Scattering Spectroscopy," Phys. Med. Biol. 42, 803–814 (1997).
45. U. Utzinger, E. V. Trujillo, E. N. Atkinson, M. F. Mitchell, S. B. Cantor, R. Richards-Kortum, "Performance Estimation of Diagnostic Tests for Cervical Pre-Cancer Based on Fluorescence Spectroscopy: Effects of Tissue Type, Sample Size, Population and Signal to Noise Ratio," IEEE Trans. Biomed. Eng. 46, 1293–1303 (1999).
46. I. J. Jacobs, R. C. Bast, "The CA-125 Tumor Associated Antigen: a Review of the Literature," Hum. Reprod. 4, 1–12 (1989).

What is claimed is:

1. A method for assessing the size of a scattering element of a sample, comprising:
   obtaining polarized reflectance spectra of the sample;
   calculating a depolarization ratio using the spectra; and
   calculating the size of the scattering element using the depolarization ratio, wherein the calculating comprises varying one or more Mie theory parameters to determine a best fit between the depolarization ratio and a combination of forward and backward scattering terms.
2. The method of claim 1, wherein the sample is in vivo.
3. The method of claim 1, wherein the sample is in vitro.
4. The method of claim 1, wherein the sample comprises cells and the scattering element comprises a cytoplasm.
5. The method of claim 1, wherein the sample comprises cells and the scattering element comprises nuclei.
6. The method of claim 5, wherein the cell comprises an epithelial cell.
7. The method of claim 5, wherein the cell comprises a cervical cell.
8. The method of claim 5, wherein the cell comprises an oral mucosa cell.
9. The method of claim 1, further comprising detecting precancer from the size of the scattering element.
10. A method for assessing the refractive index of a scattering element of a sample, comprising:
    obtaining polarized reflectance spectra of the sample;
    calculating a depolarization ratio using the spectra; and
    calculating the refractive index of the scattering element using the depolarization ratio, wherein the calculating comprises varying one or more Mie theory parameters to determine a best fit between the depolarization ratio and a combination of forward and backward scattering terms.
11. The method of claim 10, wherein the sample is in vivo.
12. The method of claim 10, wherein the sample is in vitro.
13. The method of claim 10, wherein the sample comprises cells and the scattering element comprises a cytoplasm.
14. The method of claim 10, wherein the sample comprises cells and the scattering element comprises nuclei.
15. The method of claim 14, wherein the cell comprises an epithelial cell.
16. The method of claim 14, wherein the cell comprises a cervical cell.
17. The method of claim 14, wherein the cell comprises an oral mucosa cell.
18. A method for assessing the size distribution of cell nuclei of a sample, comprising:
    obtaining polarized reflectance spectra of the sample;
    calculating a depolarization ratio using the spectra;
    varying one or more Mie theory parameters to determine a best fit between the depolarization ratio and a combination of forward and backward scattering terms; and
    determining the size of the cell nuclei using the Mie theory parameters.
19. The method of claim 18, wherein the sample is in vivo.
20. The method of claim 18, wherein the sample is in vitro.
21. The method of claim 18, wherein the cell comprises an epithelial cell.
22. The method of claim 18, wherein the cell comprises a cervical cell.
23. The method of claim 18, wherein the cell comprises an oral mucosa cell.
24. The method of claim 18, further comprising detecting precancer from the size of the cell nuclei.
25. A computer readable media containing program instructions for assessing the size of a scattering element of a sample, the computer readable media comprising:
    instructions for calculating a depolarization ratio from polarized reflectance spectra of the sample; and instructions for calculating the size of the scattering element using the depolarization ratio, wherein the calculating comprises varying one or more Mie theory parameters to determine a best fit between the depolarization ratio and a combination of forward and backward scattering terms.

* *

UNITED STATES PATENT AND TRADEMARK OFFICE
CERTIFICATE OF CORRECTION

| | | |
|---|---|---|
| PATENT NO. | : 6,639,674 B2 | Page 1 of 1 |
| APPLICATION NO. | : 09/821836 | |
| DATED | : October 28, 2003 | |
| INVENTOR(S) | : Konstantin Sokolov et al. | |

It is certified that error appears in the above-identified patent and that said Letters Patent is hereby corrected as shown below:

In the Specification

Column 1, at line 9 replace the entire paragraph with the following paragraph:

This invention was made with government support under Grant no. CA072650 awarded by the National Institutes of Health. The government has certain rights in the invention.

Signed and Sealed this
Twenty-first Day of April, 2015

Michelle K. Lee
*Director of the United States Patent and Trademark Office*